United States Patent [19]

Kamboj et al.

[11] Patent Number: 5,547,855

[45] Date of Patent: Aug. 20, 1996

[54] KAINATE-BINDING HUMAN CNS GLUTAMATE RECEPTORS EAA3C AND EAA3D, DNA ENCODING THEM, AND EXPRESSION OF THE DNA IN TRANSFORMED CELLS

[75] Inventors: Rajender Kamboj, Mississauga; Candace E. Elliott; Stephen L. Nutt, both of Etobicoke, all of Canada

[73] Assignee: Allelix Biopharmaceuticals Inc., Mississauga, Canada

[21] Appl. No.: 405,392

[22] Filed: Mar. 15, 1995

Related U.S. Application Data

[63] Continuation of Ser. No. 989,793, Dec. 11, 1992, abandoned.

[51] Int. Cl.$^6$ .............................. C12N 15/12; C12N 5/10; C07K 14/705; C08L 89/00
[52] U.S. Cl. .................. 435/69.1; 435/320.1; 435/240.2; 435/252.3; 435/254.11; 435/317.1; 536/23.5; 530/350; 530/395
[58] Field of Search .............................. 435/69.1, 320.1, 435/240.2, 252.3, 254.11, 317.1; 536/23.5; 530/350, 395

[56] References Cited

U.S. PATENT DOCUMENTS 5,202,257  4/1993  Heinemann et al. ................ 435/252.3

FOREIGN PATENT DOCUMENTS 0529995  3/1993  European Pat. Off. .
0529994  3/1993  European Pat. Off. .
WO91/06648  5/1991  WIPO .

OTHER PUBLICATIONS

Better et al. (1992) *Neuron* 8: 257–264 "Cloning of a Putative Glutamate Receptor: A Low Affinity Kainate–Binding Subunit".

Egebjerg et al. (1991) *Nature* 351: 745–748 "Cloning of a cDNA for a glutamate receptor subunit activated by kainate but not AMPA".

Eshhar et al. (1992) *FEBS* 297: 257–262 "Structural characterization and expression of a brain specific gene encoding chick kainate binding protein".

Gregor et al. (1989) *Nature* 342: 689–692 "Molecular structure of the chick cerebellar kainate–binding subunit of a putative glutamate receptor".

Oksenberg et al. (1992) *Nature* 360: 161–163 "A single amino–acid difference confers major pharmacological variation between human and rodent 5–HT$_{1B}$ receptors".

Sakimura et al. (1992) *Neuron* 8: 267–274 "Primary Structure and Expression of the 2 Subunit of the Glutamate Receptor Channel Selective for Kainate".

Wada et al. (1989) *Nature* 342: 684–689 "Sequence and expression of a frog brain complementary DNA encoding a kainate–binding protein".

Werner et al. (1991) *Nature* 351: 742–744 "Cloning of a putative high–affinity kainate receptor expressed predominantly in hippocampal CA3 cells".

Sugmara et al., Structures and Properties of Seven Isoforms of the NMDA Receptor Generated by Alternative Splicing, Institute for Immunology, Kyoto University Faculty of Medicine, Sakyo–ku, Kyoto 606, Japan, vol. 185, No. 3, pp. 826–832 (Jun. 30, 1992).

Carmie Puckett, et al., "Molecular cloning and chromosomal localization of one of the human glutamate receptor genes"; Proc. Natl. Acad. Sci. USA, vol. 88, pp. 7557–7561, Sep. 1991.

Sun et al., "Molecular Cloning, Chromosomal Mapping, and Functional Expression of Human Brain Glutamate Receptors," Proc. Natl. Acad. Sci., vol. 89, pp. 1443–1447 (Feb. 1992).

Bochet, P., et al. (1993) *EXS* (Basel) 63: 224–233.
Bettler, B., et al. (1990) *Neuron* 5: 383–395.
Sambrook, J., et al. (1989) Molecular Cloning: a laboratory manual, Cold Spring Harbor Press, Chapter 11 (selected pages included).

Primary Examiner—Garnette D. Draper
Assistant Examiner—David L. Fitzgerald
Attorney, Agent, or Firm—Foley & Lardner

[57] ABSTRACT

Neurotransmission by excitatory amino acids (EAAs) such as glutamate is mediated via membrane-bound surface receptors. DNA coding for one family of the kainate-binding type of EAA receptor, has now been isolated and the receptor protein characterized. Herein described are recombinant cell lines which produce the EAA receptor as a heterologous membrane-bound product. Disclosed is use of the cell lines as a tool for discovery of compounds which modulate EAA receptor stimulation.

24 Claims, 16 Drawing Sheets

FIG. IA

```
EcoRI
    GAATTCCGTCTCTTCCCCCTTTCCCTCTGTCTGTGCCTATCCCCGACTTTTGC
1   -----+---------+---------+---------+---------+---------+   60
    CTTAAGGCAGAGAAGAAAGGGGGAAAAGGGAGAGACAGACGGATAGGGGCTGAAAACG

ATCTGACCAAAGGACGAATGAGGAGACGTTCCTGCAGATCGGGGCAGCAACTTTCCTCA
61  -----+---------+---------+---------+---------+---------+  120
    TAGACTGGTTTCCTGCTTACTCCCTCTGCAAGGACGTCTAGCCCCGTCGTTGAAAGGAGT

GCTGGTCTCTGGGCTCCGGAGCCAGAGAGCGCTGATCCTCCGCGTCTGCGGCCATGAAG
121 -----+---------+---------+---------+---------+---------+  180
    CGACCAGAGACCCGAGGCCTCGGTCTCTCGCGACTAGGAGGCGCAGACGCCGGGTACTTC

AGAGAGAGAGCCGTGATGGGCTAGCGACACTGAGGAGCCCCGAGAGAGCTCAGCCTT
181 -----+---------+---------+---------+---------+---------+  240
    TCTCTCTCTCGGCACTACCCGATCGCTGTCGTGACTCCTCGGGCTCTCTCGAGTCGGAA

GCCAGCCAGCTCCGCGGTCCCACGCGGGTTCCCTCGAGCTCGTCCGTGGGGAGCGGCA
241 -----+---------+---------+---------+---------+---------+  300
    CGGTCGGTCGAGGCGCCAGGGTGCGCCCAAGGAGCTCGAGCGAGGCACCCCTCGCGCGT

GCGTGCTTGAACCGGAGCATCCAGAGAGGATGAGGCGGGGACCCGGCCAAGTTGGGTG
301 -----+---------+---------+---------+---------+---------+  360
    CGCACGAACCTTGGCCTCGTAGGTCTCTCCTACTCCGCCCCTGGCCGGGTTCAACCCAC

CATCTCTCGGGCGTCCGGCAGCAGCCTGTATCTCGGCATGAATTAAGAAGCTAGGAAGATG
361 -----+---------+---------+---------+---------+---------+  420
    GTAGAGAGCCCGCAGGCCGTCGCCGACATAGAGCCGTACTTAATTCTTCGATCCTTCTAC
                                        M                       -30
```

FIG. 1B

```
421  GAGCACGGCACACTCCTCGCCCAGCCCGGCTCTGGACCCAGGACACCAGCTGGGCACTC
     ---------+---------+---------+---------+---------+---------+  480
     CTCGTGCCGTGTGAGGAGCGGGTCGGGCCGAGACCTGGTCCCTGTGGTCGACCCGTGAG
-29   E  H  G  T  L  L  A  Q  P  G  L  W  T  R  D  T  S  W  A  L   -10

481  CTCTATTTCCTCTGCTATATCCCTCCTCAGACCGCCCCGCAAGTACTCAGGATCGGAGGG
     ---------+---------+---------+---------+---------+---------+  540
     GAGATAAAGGAGACGATATAGGAGGAGTCTGGCGGGGCGTTCATGAGTCCTAGCCTCCC
-09   L  Y  F  L  C  Y  I  L  P  Q  T  A  P  Q  V  L  R  I  G  G    11
                                    |_ Mature Amino-Terminal 541  ATTTTTGAAACAGTGGAAAATGAGCCTGTTAATGTTGAAGAATTAGCTTTCAAGTTTGCA
     ---------+---------+---------+---------+---------+---------+  600
     TAAAAACTTTGTCACCTTTTACTCGGACAATTACAACTTCTTAATCGAAAGTTCAAACGT
 12   I  F  E  T  V  E  N  E  P  V  N  V  E  E  L  A  F  K  F  A    31

601  GTCACCAGCATTAACAGAAACAGAAACCGAACCCTGATGCCTAACACCACTTAACCTATGACATC
     ---------+---------+---------+---------+---------+---------+  660
     CAGTGGTCGTAATTGTCTTTGCTTGGACTACGGATTGTGGTAATTGGATACTGTAG
 32   V  T  S  I  N  R  N  R  T  L  M  P  N  T  T  L  T  Y  D  I    51

661  CAGAGAATTAACCTTTTTGATAGTTTTGAAGCCTCGCGGAGAGCATGTGACCAGCTGGCT
     ---------+---------+---------+---------+---------+---------+  720
     GTCTCTTAATTGGAAAAACTATCAAAACTTCGGAGCGCCTCGTACACTGGTCGACCGA
 52   Q  R  I  N  L  F  D  S  F  E  A  S  R  R  A  C  D  Q  L  A    71

721  CTTGGTGTGGCTGCTCTCTTTGGCCCTTCCCATAGCTCTCCGTCAGTGTGTGCAGTCT
     ---------+---------+---------+---------+---------+---------+  780
     GAACCACACCGACGAGACTGAGAACCGGGTATCGAGGAGGCAGTCACGACACGTCAGA
 72   L  G  V  A  A  L  F  G  P  S  H  S  S  S  V  S  A  V  Q  S    91
```

FIG. IC

```
781  ATTTGCAATGCTCTCGAAGTTCCACACATACAGACCCCTGAAACACCCCTCGGTGTGGAC   840
     ----+----+----+----+----+----+----+----+----+----+----+----+
     TAAACGTTACGAGAGCTTCAAGGTGTGTATGTCTGTGGGACCTTTGTGGGAGCCACCTG
 92   I  C  N  A  L  E  V  P  H  I  Q  T  R  W  K  H  P  S  V  D    111

841  AACAAAGATTGTTTACATCAACCTTTACCCAGATTATGCAGCTATCAGCAGGGCGATC   900
     ----+----+----+----+----+----+----+----+----+----+----+----+
     TTGTTTCTAACAAATGTAGTTGGAAATGGGTCTAATACGTCGATAGTCGTCCCGCTAG
112   N  K  D  L  F  Y  I  N  L  Y  P  D  Y  A  A  I  S  R  A  I    130

901  CTGGATCTGGTCCTCTATTACAACTGGAAAACAGTGACAGTGGTGTATGAAGACAGCACA   960
     ----+----+----+----+----+----+----+----+----+----+----+----+
     GACCTAGACCAGGAGATAATGTTGACCTTTTGTCACTGTCACCACATACTTCTGTCGTGT
132   L  D  L  V  L  Y  Y  N  W  K  T  V  T  V  V  Y  E  D  S  T    150

961  GGTCTAATTCGTCTACAAGAGCTCATCAAAGCTCCCTCCAGATATAATATTAAAATCAAA  1020
     ----+----+----+----+----+----+----+----+----+----+----+----+
     CCAGATTAAGCAGATGTTCTCGAGTAGTTTCGAGGGAGGTCTATATTATAATTTTAGTTT
152   G  L  I  R  L  Q  E  L  I  K  A  P  S  R  Y  N  I  K  I  K    170

1021 ATCCGCCAGCTGCCCTGGGAATAAAGATGCCAAGCCTTTACTCAAGGAGATGAAGAAA  1080
     ----+----+----+----+----+----+----+----+----+----+----+----+
     TAGGCGGTCGACGGGAGACCCTTATTCTACGGTTCGGAAATGAGTTCCTCTACTTCTTT
172   I  R  Q  L  P  S  G  N  K  D  A  K  P  L  L  K  E  M  K  K    190

1081 GGCAAGGAGGAGTTCTATGTGATATTTGATTGTTCACATGAAACAGCCGCTGAAATCCTTAAG  1140
     ----+----+----+----+----+----+----+----+----+----+----+----+
     CCGTTCCTCCTCAAGATACACTATAAACTAACAAGTGTACTTTGTCGGCGACTTTAGGAATTC
192   G  K  E  F  Y  V  I  F  D  C  S  H  E  T  A  A  E  I  L  K    211
```

FIG. 1D

```
1141  CAGATTCTGTTCATGGGCATGATGACCGAATACTATCACTACTTTTTCACAACCCTGGAC  1200
      ------+---------+---------+---------+---------+---------+
      GTCTAAGACAAGTACCCGTACTACTGGCTTATGATAGTGATGAAAAAGTGTTGGGACCTG
212   Q   I   L   F   M   G   M   M   T   E   Y   Y   H   Y   F   F   T   T   L   D   231

1201  TTATTTGCTTTGGATCTGGAACTCTATAGGTACAGTGGCGTAAACATGACCGGGTTTGGG  1260
      ------+---------+---------+---------+---------+---------+
      AATAAACGAAACCTAGACCTTGAGATATCCATGTCACCGCATTTGTACTGGCCCAAACCC
232   L   F   A   L   D   L   E   L   Y   R   Y   S   G   V   N   M   T   G   F   G   251

1261  CTGCTTAACATTGACAACCCTCACGTGTCATCCATCATTGAGAAGTGGTCCATGGAGAGA  1320
      ------+---------+---------+---------+---------+---------+
      GACGAATTGTAACTGTTGGGAGTGCACAGTAGTAACTCTTCACCAGTACCTCTCT
252   L   L   N   I   D   N   P   H   V   S   S   I   I   E   K   W   S   M   E   R   271

1321  CTGCAGGCCCCACCCCGAGGCCCTTTTGGATGCATGATGACAACTGAAGCG  1380
      ------+---------+---------+---------+---------+---------+
      GACGTCCGGGGTGGGGCTCTGGGCCTCTGACCGGAAAACCTACCTACTGTTGACTTCGC
272   L   Q   A   P   P   R   P   E   T   G   L   L   D   G   M   M   T   E   A   291

1381  GCTCTCGATGTACGATGCTGTGTACATGGTGGCCATTGCCTCGCACCGGGCATCCCAGCTG  1440
      ------+---------+---------+---------+---------+---------+
      CGAGACTACATGCTACGACACATGTACCACCGGTAACGGAGCCCGTAGGGTCGAC
292   A   L   M   Y   D   A   V   Y   M   V   A   I   A   S   H   R   A   S   Q   L   311

1441  ACCGTCAGCTCCCTGCAGTGCCATAGACATAAGCCATGGCGCCTCGGACCCAGATTATG  1500
      ------+---------+---------+---------+---------+---------+
      TGGCAGTCGAGGGACGTCACGGTATCTGTATTCGGTACCGCGGAGCCTGGGTCTAAATAC
312   T   V   S   S   L   Q   C   H   R   H   K   P   W   R   L   G   P   R   F   M   331
```

FIG. 1E

```
1501 AACCTGATCAAAGAGGCCCGGTGGGATGGCTTGACTGGGCATATCACCTTTAATAAACC   1560
     ----+----+----+----+----+----+----+----+----+----+----+----+
     TTGGACTAGTTTCTCCGGGCCACCCTACCGAACTGACCCGTATAGTGGAAATTATTTGG
332    N  L  I  K  E  A  R  W  D  G  L  T  G  H  I  T  F  N  K  T  351

1561 AATGGCTTGAGGAAGGATTTTGATCTGGACATTATTAGTCTCAAAGAGGAAGGAACTGAA   1620
     ----+----+----+----+----+----+----+----+----+----+----+----+
     TTACCGAACTCCTTCCTAAAACTAGACCTGTAATAATCAGAGTTTCTCCTTCCTTGACTT
352    N  G  L  R  K  D  F  D  L  D  I  I  S  L  K  E  E  G  T  E  371

1621 AAGATTGGGATTTGGAATTCCAACAGTGGCTTAACATGACGGACAGCAACAAAGACAAG   1680
     ----+----+----+----+----+----+----+----+----+----+----+----+
     TTCTAACCCTAAACCTTAAGGTTGTCACCCGAATTGTACTGCCTGTCGTTGTTTCTGTTC
372    K  I  G  I  W  N  S  N  S  G  L  N  M  T  D  S  N  K  D  K  391

1681 TCCAGCAATATCACTGATTCATTGGCCAACAGAACACTCATTGTCACCACCATTCTGGAA   1740
     ----+----+----+----+----+----+----+----+----+----+----+----+
     AGGTCGTTATAGTGACTAAGTAACCGGTTGTCTTGTGAGTAACAGTGGTGGTAAGACCTT
392    S  S  N  I  T  D  S  L  A  N  R  T  L  I  V  T  T  I  L  E  411

1741 GAACCCTATGTTATGTACAGGAAATCTGATAAGCCCTCTATATGGAAATGACAGATTTGAA   1800
     ----+----+----+----+----+----+----+----+----+----+----+----+
     CTTGGGATACAATACATGTCCTTTAGACTATTCGGAGATATACCTTTACTGTCTAAACTT
412    E  P  Y  V  M  Y  R  K  S  D  K  P  L  Y  G  N  D  R  F  E  431

1801 GGATATTGCCTAGACCTGTTGAAAGAATTGTCAAACATCCTGGGTTTCATTTATGATGTT   1860
     ----+----+----+----+----+----+----+----+----+----+----+----+
     CCTATAACGGATCGGACAACTTTCTTAACAGTTGTAGGACCCAAAGTAAATACTACAA
432    G  Y  C  L  D  L  L  K  E  L  S  N  I  L  G  F  I  Y  D  V  451
```

FIG. 1F

```
1861  AAACTAGTTCCCGATGGCAAATATGGGGCCCAGAATGACAAAGGGAGTGGAACGGGATG
      ------+---------+---------+---------+---------+---------+  1920
      TTTGATCAAGGGCTACCGTTTATACCCCGGGTCTTACTGTTTCCCCTCACCTTGCCCTAC
 452  K   L   V   P   D   G   K   Y   G   A   Q   N   D   K   G   E   W   N   G   M       471

1921  GTTAAAGAACTCATAGATCACAGGGCTGACCTGGCAGTGCCTCTCTTACCATCACCTAC
      ------+---------+---------+---------+---------+---------+  1980
      CAATTTCTTGAGTATCTAGTGTCCCGACTGGACCGTCACGGAGAGAATGGTAGTGGATG
 472  V   K   E   L   I   D   H   R   A   D   L   A   V   A   P   L   T   I   T   Y       491

1981  GTGCGGGAGAAAGTCATTGACTTCTCCAAACCCTTCATGACCCTAGGCATCAGCATTCTC
      ------+---------+---------+---------+---------+---------+  2040
      CACGCCCTCTTTCAGTAACTGAAGAGGTTTGGGAAGTACTGGGATCCGTAGTCGTAAGAG
 492  V   R   E   K   V   I   D   F   S   K   P   F   M   T   L   G   I   S   I   L       511

2041  TACCGGAAGCCCAATGGTACCAATCCAGGCGTTTCTCCTTCAACCCCCCTGTCTCTCCA
      ------+---------+---------+---------+---------+---------+  2100
      ATGGCCTTCGGGTTACCATGGTTAGGTCCGCAAAGAGGAAGGAGTTGGGGACAGAGGT
 512  Y   R   K   P   N   G   T   N   P   G   V   F   S   F   L   N   P   L   S   P       531

2101  GATATTTGGATGTATGTGCTCTTAGCCTGCTTGGGAGTCAGCTGTGTACTCTTTGTGATT
      ------+---------+---------+---------+---------+---------+  2160
      CTATAAACCTACATACACGAGAATCGGACGAACCCTCAGTCGACACATGAGAAACACTAA
 532  D   I   W   M   Y   V   L   L   A   C   L   G   V   S   C   V   L   F   V   I       551

2161  GCAAGGTTTACACCCTACGAGTGGTATAAACCCCACCATGCAACCCTGACTCAGACGTg
      ------+---------+---------+---------+---------+---------+  2220
      CGTTCCAAATGTGGGATGCTCACCATATTGGGGTACGTTGGGACTGAGTCTGCAc
 552  A   R   F   T   P   Y   E   W   Y   N   P   H   P   C   N   P   D   S   D   V       571
```

FIG. 1G

```
2221  GTGGAAACAATTTACTTACTAAATAGTTTCTGGTTTGGAGTTGGAGCTCTCATGCAG  2280
      ----+----+----+----+----+----+----+----+----+----+----+----+
      CACCTTTGTTAAATGAATGATTTATCAAAGACCAAACCTCAACCTCGAGAGTACGTC
572   V  E  N  N  F  T  L  N  S  F  W  F  G  V  G  A  L  M  Q     591

2281  CAAGGATCAGAGCTGATGCCCAAAGCTCTATCGACCAGAATAGTTGGAGGATATGGTGG  2340
      ----+----+----+----+----+----+----+----+----+----+----+----+
      GTTCCTAGTCTCGACTACGGGTTTCGAGATAGCTGGTCTTATCAACCTCCCTATACCACC
592   Q  G  S  E  L  M  P  K  A  L  S  T  R  I  V  G  G  I  W  W   611

2341  TTTTTCACCCTAATCATCATTTCATCCTACACGGCCAATCTGGCTGCCTTCTTGACAGTA  2400
      ----+----+----+----+----+----+----+----+----+----+----+----+
      AAAAGTGGGATTAGTAGTAAAGTAGGATGTGCCGGTTAGACCGACGGAAGAACTGTCAT
612   F  F  T  L  I  I  I  S  S  Y  T  A  N  L  A  A  F  L  T  V   631

2401  GAGAGAATGGAATCCCCCATAGAATTCGGCAGATGATCAACAATGACCTTCTTCAAGAAATCAAAAATCTCCACC  2460
      ----+----+----+----+----+----+----+----+----+----+----+----+
      CTCTCTTACCTTAGGGGTATCTAAGCCGTCTACTAGTTGTTACTGGAAGAAGTTCTTTAGTTTTTAGAGGTGG
632   E  R  M  E  S  P  I  D  S  A  D  D  L  A  K  Q  T  K  I  E   651

2461  TATGGGGCGGTTAGAGAGATGGATCAACAATGACCTTCTTCAAGAAATCAAAAATCTCCACC  2520
      ----+----+----+----+----+----+----+----+----+----+----+----+
      ATACCCCGCCAATCTCTCTACCTAGTTGTTACTGGAAGAAGTTCTTTAGTTTTTAGAGGTGG
652   Y  G  A  V  R  D  G  S  T  M  T  F  F  K  K  S  K  I  S  T   671

2521  TATGAGAAGATGTGGGCTTTCATGAGCAGCAGGCAGCAGACCGCCCTGGTAAGAAACAGT  2580
      ----+----+----+----+----+----+----+----+----+----+----+----+
      ATACTCTTCTACACCCGAAAGTACTCGTCGTCCGTCGTCTGGCGGGACCATTCTTTGTCA
672   Y  E  K  M  W  A  F  M  S  S  R  Q  Q  T  A  L  V  R  N  S   691
```

FIG. 1H

```
2581  GATGAGGGGATCCAGAGAGTGCTCACCAGAGACTACGCGCTGCTGATGGAGTCCACCAGC  2640
      ------+---------+---------+---------+---------+---------+
      CTACTCCCCTAGGTCTCTCACGAGTGGTCTCGATGCGCGACGACTACCTCAGGTGGTCG
 692  D  E  G  I  Q  R  V  L  T  T  D  Y  A  L  L  M  E  S  T  S   711

2641  ATTGAGTATGTGACGCAGAGAAACTGCAACCTCACTCAGATCGGGGCCCTCATTGACTCC  2700
      ------+---------+---------+---------+---------+---------+
      TAACTCATACACTGCGTCTCTTTGACGTTGGAGTGAGTCTAGCCCCGGGAGTAACTGAGG
 712  I  E  Y  V  T  Q  R  N  C  N  L  T  Q  I  G  G  L  I  D  S   731

2701  AAAGGTTACGGAGTGGGAACACCTATTGGTTCTCCTTACCGGGATAAAATTACTATTGCT  2760
      ------+---------+---------+---------+---------+---------+
      TTTCCAATGCCTCACCCTTGTGGATAACCAAGAGGAATGGCCCTATTTTAATGATAACGA
 732  K  G  Y  G  V  G  T  P  I  G  S  P  Y  R  D  K  I  T  I  A   751

2761  ATTCTTCAACTCCAAGAAGGAAGCTGCATATGATGAAAGAGAAGTGGTGGCGTGGG      2820
      ------+---------+---------+---------+---------+---------+
      TAAGAAGTTGAGGTTCTTCCCTTCGACGTATACTACTTTCTCTTCACCACCGCACCC
 752  I  L  Q  E  E  G  K  L  H  M  M  K  E  K  W  R  G           771

2821  AATGGCTGCCCCGAGGAAGACAACAAAGAAGCCAGTGCCCTGGGAGTGGAAAATATTGGA  2880
      ------+---------+---------+---------+---------+---------+
      TTACCGACGGGGCTCCTTCTGTTGTTTCTTCGGTCACGGGACCCTCACCTTTTATAACCT
 772  N  G  C  P  E  E  D  N  K  E  A  S  A  L  G  V  E  N  I  G   791

2881  GGCATCTTCATTGTTCTGGCTGCCGGACTGGTCCTTTCTGTATTGTAGCTATTGGAGAA   2940
      ------+---------+---------+---------+---------+---------+
      CCGTAGAAGTAACAAGACGACGGCCTGACCAGGAGAAAGACATAACATCGATAACCTCTT
 792  G  I  F  I  V  L  A  A  G  L  V  L  S  V  F  V  A  I  G  E   811
```

FIG. 11

```
2941  TTCATATACAAATCACGGAAGAATAATGATATTGAACAGTGTCTCTCTTTCAACGCTATC  3000
      ----+----+----+----+----+----+----+----+----+----+----+----+
      AAGTATATGTTTAGTGCCTTCTTATTACTATAACTTGTCACAGAGAGAAAGTTGCGATAG
812    F  I  Y  K  S  R  K  N  N  D  I  E  Q  C  L  S  F  N  A  I  831

3001  ATGGAAGAACTGGGAATCTCACTGAAGAATCAGAAAAATAAAGAAAAAAGTCAAGAACT   3060
      ----+----+----+----+----+----+----+----+----+----+----+----+
      TACCTTCTTGACCCTTAGAGTGACTTCTTAGTCTTTTATTTCTTTTTTCAGTTCTTGA
832    M  E  E  L  G  I  S  L  K  N  Q  K  K  I  K  K  K  S  R  T  851

3061  AAGGGGAAATCTTCCTTCACAAGTATCCTTACTGTTCATCAGAGACGAACTCAGAGAAAA  3120
      ----+----+----+----+----+----+----+----+----+----+----+----+
      TTCCCCTTTAGAAGGAAGTGTTCATAGGAATGAACAGTAGTCTCTGCTTGAGTCTCTTTT
852    K  G  K  S  S  F  T  S  I  L  T  C  H  Q  R  R  T  Q  R  K  871

3121  GAGACTGTGGCGTGATCCAAGGAAACGCCTGTAGGAAGAAAAAGGATGCATTCCCTACAG  3180
      ----+----+----+----+----+----+----+----+----+----+----+----+
      CTCTGACACCGCACTAGGTTCCTTTGCGGACATCCTTCTTTTTCCTACGTAAGGGATGTC
872    E  T  V  A  875
```

FIG.1J

```
3181  ATTTTTGGAGAAAGGATTTCTGAGGAGTTGTGTGATGTGTTTCCATATATCTATATCCAT
      ----+----+----+----+----+----+----+----+----+----+----+----+   3240
      TAAAAACCTCTTCCTAAAGACTCCTCAACACACTACACAAAGGTATATAGATATAGGTA

3241  AACTCTGATTATGAATACAGATATAAGAAATACAAAAGTTTAAAAGCTCACATAGATAT
      ----+----+----+----+----+----+----+----+----+----+----+----+   3300
      TTGAGACTAATACTTATGTCTATATTCTTTATGTTTTTCAAATTTTTCGAGTGTATCTATA

3301  GACTTGGGAAGTGACACCAGTTCTTTTTAAAATAAATTTGTATGCACAAAAAAAAAAAA
      ----+----+----+----+----+----+----+----+----+----+----+----+   3360
      CTGAACCCTTCACTGTGGTCAAGAAAATTTATTTAAACATACGTGTTTTTTTTTTTTT

EcoRI
                --
3361  AAAAAAAAAAAAAAAAAAAAAGGAATTC         3385
      ----+----+----+----+----+----
      TTTTTTTTTTTTTTTTTTTTTCCTTAAG
```

FIG. 4A

AMINO ACID SEQUENCE:

```
HumEAA3b  626  AAFLTVERMESPINSADDLAKQTKIEYGAVRDGSTMTFFKKSKISTYEKM  675
               ||||||||||||||| |||||||||||||||||||||||||||||||||
HumEAA3a  626  AAFLTVERMESPIDSADDLAKQTKIEYGAVRDGSTMTFFKKSKISTYEKM  675
```

NUCEOTIDE SEQUENCE:

```
HumEAA3b  2402  GAGAGAATGGAATCCCCCATAAATTCGGGCAGATGATCTGGCAAAGCAAAC  2451
                ||||||||||||||||||||| ||| |||||||||||||||||||||||
HumEAA3a  2402  GAGAGAATGGAATCCCCCATAGATTCGGCAGATGATCTGGCAAAGCAAAC  2451
```

FIG. 4B

AMINO ACID SEQUENCE:

```
HumEAA3c  798  AAGLVLSVFVAIGEFIYKSRKNNDIEQVSHLFLGLVSL*............         835
               ||||||||||||||||||||||||||||||||| ::  .:
HumEAA3a  798  AAGLVLSVFVAIGEFIYKSRKNNDIEQCLSFNAIMEELGISLKNQKKIKK          847
```

NUCLEOTIDE SEQUENCE:

```
HumEAA3c  2950  CAAATCACGGAAGAATAATGATATTGAACAG......GTGAGTCATCTCTT          2994
                |||||||||||||||||||||||||||||||      ||  ||| ||| ||
HumEAA3a  2950  CAAATCACGGAAGAATAATGATATTGAACAGTGTCTCTTCAACGCTA              2999

HumEAA3c  2995  TCTAGGACTGGTTAGTTTATAGTTTGCATTATCTGTCTTAAGTTTGGGGG           3044
                || || ||| || ||  |  ||| ||  |||| --|| |||  |   -
HumEAA3a  3000  TCATGGAAGAACTGGGAATCTCACTGAAGAATCAGAAAAAATAAAGAAA           3049

HumEAA3c  3045  TTTTTAAGGATGTTTGCTCTTTTT                                     3069
                    ||| || |  || |||
HumEAA3a  3050  AAGTCAAGAACTAAGGGGAAATCT                                     3074
```

FIG. 4C

AMINO ACID SEQUENCE:

```
          |------ Signal Peptide ------|--  Mature Protein
                                       1
HumEAA3d  -30  MEHGTLLAQPGLWTRDTSWGLLYFLCYILPQTAPQ..............    5
                |||||||||||||||||||||||||||||||||||
HumEAA3a  -30  MEHGTLLAQPGLWTRDTSWGLLYFLCYILPQTAPQVLRIGGIFETVENEP   20

HumEAA3d    6  ...............................VLRIACDQL             14
                                               |||||||||
HumEAA3a   21  VNVEELAFKFAVTSINRNRTLMPNTTLTYDIQRINLFDSFEVLRIACDQL    70
```

NUCLEOTIDE SEQUENCE:

```
HumEAA3d  500  ATCCCTCCCTCAGACCGCCCCGCAAGTACTCAGGATC.............   535
               |||||||||||||||||||||||||||||||||||||
HumEAA3a  500  ATCCCTCCCTCAGACCGCCCCGCAAGTACTCAGGATCTCAGGAGGATTTTGA 549

HumEAA3d  536  .....GCATGTGACCAGCTGCTCTTGGTGTGGCTGCTCTCTTTGGCCCCTT   581
                    ||||||||||||||||||||||||||||||||||||||||||||||
HumEAA3a  700  GAGAGCATGTGACCAGCTGCTCTTGGTGTGGCTGCTCTCTTTGGCCCCTT    749
```

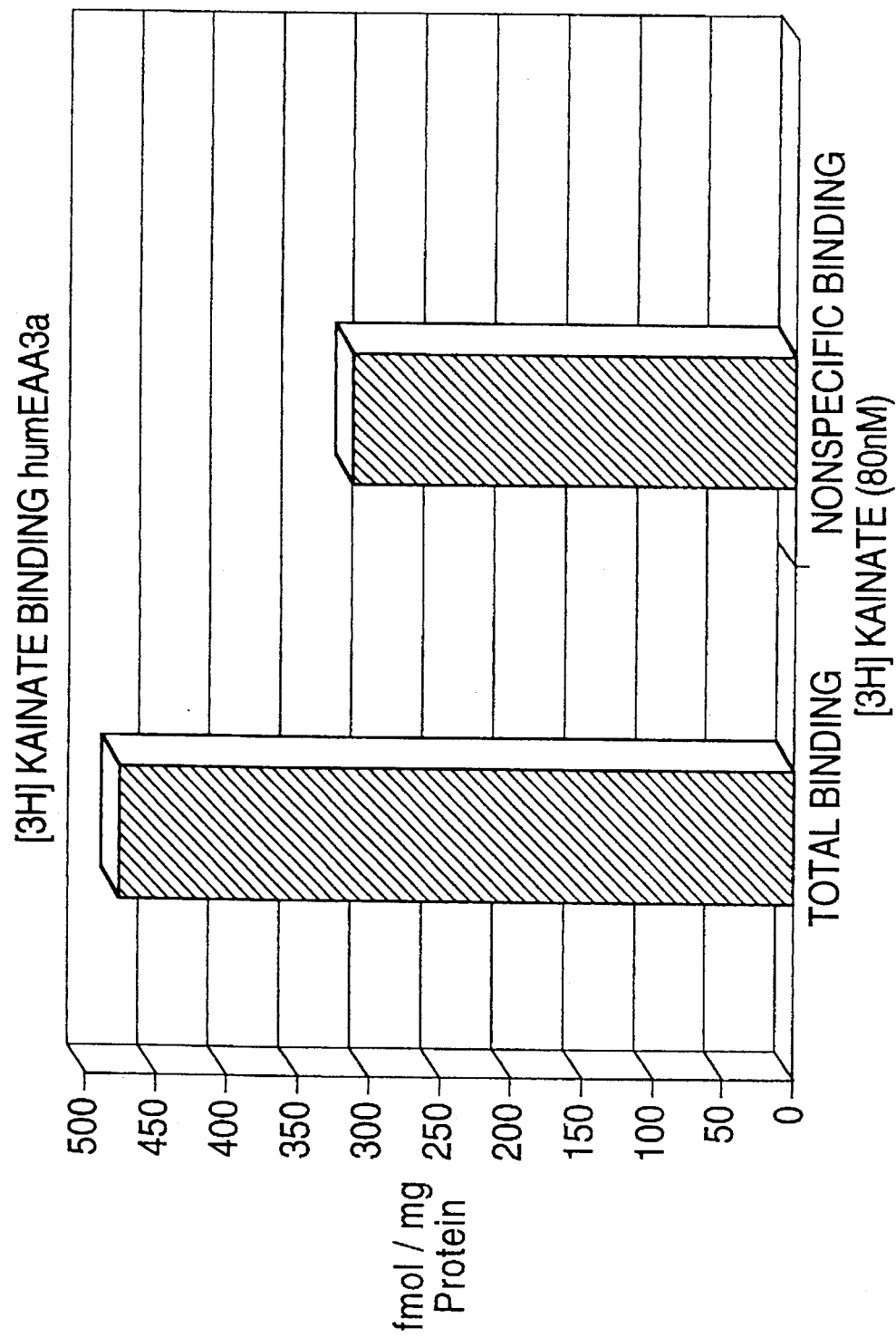

KAINATE-BINDING HUMAN CNS GLUTAMATE RECEPTORS EAA3C AND EAA3D, DNA ENCODING THEM, AND EXPRESSION OF THE DNA IN TRANSFORMED CELLS

This application is a continuation of application Ser. No. 07/989,793, filed Dec. 11, 1992, now abandoned.

FIELD OF THE INVENTION

This invention is concerned with applications of recombinant DNA technology in the field of neurobiology. More particularly, the invention relates to the cloning and expression of DNA coding for excitatory amino acid (EAA) receptors, especially human EAA receptors.

BACKGROUND TO THE INVENTION

In the mammalian central nervous system (CNS), the transmission of nerve impulses is controlled by the interaction between a neurotransmitter substance released by the "sending" neuron which then binds to a surface receptor on the "receiving" neuron, to cause excitation thereof. L-glutamate is the most abundant neurotransmitter in the CNS, and mediates the major excitatory pathway in vertebrates. Glutamate is therefore referred to as an excitatory amino acid (EAA) and the receptors which respond to it are variously referred to as glutamate receptors, or more commonly as EAA receptors.

Using tissues isolated from mammalian brain, and various synthetic EAA receptor agonists, knowledge of EAA receptor pharmacology has been refined somewhat. Members of the EAA receptor family are now grouped into three main types based on differential binding to such agonists. One type of EAA receptor, which is addition to glutamate also binds the agonist NMDA (N-methyl-D-aspartate), is referred to as the NMDA type of EAA receptor. Two other glutamate-binding types of EAA receptor, which do not bind NMDA, are named according to their preference for binding with two other EAA receptor agonists, namely AMPA (α-amino-3-hydroxy-5-methyl-isoxazole-4-propionate), and kainate. Particularly, receptors which bind glutamate but not NMDA, and which bind with greater affinity to kainate than to AMPA, are referred to as kainate type EAA receptors. Similarly, those EAA receptors which bind glutamate but not NMDA, and which bind AMPA with greater affinity than kainate are referred to as AMPA type EAA receptors.

The glutamate-binding EAA receptor family is of great physiological and medical importance. Glutamate is involved in many aspects of long-term potentiation (learning and memory), in the development of synaptic plasticity, in epileptic seizures, in neuronal damage caused by ischemia following stroke or other hypoxic events, as well as in other forms of neurodegenerative processes. However, the development of therapeutics which modulate these processes has been very difficult, due to the lack of any homogeneous source of receptor material with which to discover selectively binding drug molecules, which interact specifically at the interface of the EAA receptor. The brain derived tissues currently used to screen candidate drugs are heterogeneous receptor sources, possessing on their surface many receptor types which interfere with studies of the EAA receptor/ligand interface of interest. The search for human therapeutics is further complicated by the limited availability of brain tissue of human origin. It would therefore be desirable to obtain cells that are genetically engineered to produce only the receptor of interest. With cell lines expressing cloned receptor genes, a substrate which is homogeneous for the desired receptor is provided, for drug screening programs.

Non-human cDNAs which appear to encode the kainate-type of receptor have been reported. Egebjerg et al. (nature 351:745, 1991) and WO91/06648, each describe the isolation of a cDNA from rat called GluR6 which, although related by sequence to AMPA receptor genes, forms a receptor which is not activated by AMPA but rather by glutamate, quisqualate, and preferentially, kainate. Other kainate binding proteins, which do not readily exhibit ion channel properties when expressed in a homomeric fashion, have also been cloned from frog (Wada et al., Nature 342: 684, 1989), chicken (Gregor et al., Nature 342: 689, 1989; Eshar et al., FEBS Lett. 297: 257, 1992), mouse (Sakimura et al., Neuron 8: 267, 1992) and rat (Werner et al., Nature 351: 742, 1991; Bettler et al., Neuron 8: 257, 1992; Herb et al., Neuron 8: 775, 1992).

There has emerged from these molecular cloning advances a better understanding of the structural features of EAA receptors and their subunits, as they exist in the rat brain. According to the current model of EAA receptor structure, each is heteromeric in structure, consisting of individual membrane-anchored subunits, each having four transmembrane regions, and extracellular domains that dictate ligand binding properties to some extent and contribute to the ion-gating function served by the receptor complex.

In the search for therapeutics useful to treat CNS disorders in humans, it is highly desirable to obtain knowledge of human EAA receptors. A specific understanding of human receptors would provide a means to screen for compounds that react therewith, i.e. to stimulate or inhibit receptor activity, and thus, provides a means to identify compounds having potential therapeutic utility in humans. Non-human mammalian models are not suitable for this purpose despite significant receptor sequence homology as minute sequence differences between species homologues of the same receptor from different species can cause dramatic pharmacological variation (Oksenberg et al., Nature, 360: 161, 1992). It is therefore particularly desirable to provide cloned cDNA encoding human EAA receptors, and cell lines expressing these receptors in a homogeneous fashion, in order to generate a proper screening method for compounds therapeutically useful in humans. These, accordingly, are objects of the present invention.

It is another object of the present invention to provide in isolated form a DNA molecule which codes for a human EAA receptor.

It is another object of the present invention to provide a cell that has been genetically engineered to produce a kainate-binding human EAA receptor.

Other objects of the present invention will be apparent from the following description of the invention.

SUMMARY OF THE INVENTION

Polynucleotides coding for a family of EAA receptors which in addition to binding glutamate with an affinity typical of EAA receptors, also exhibit ligand binding properties characteristic of kainate-type EAA receptors, have now been identified and characterized. A representative member of this human EAA receptor family is herein designated human EAA3a. Sequence-related polynucleotides coding for naturally occurring variants of the human EAA3a receptor have also been identified, and constitute additional members of this receptor family, herein referred to as the human EAA3 receptor family.

The present invention thus provides, in one of its aspects, an isolated polynucleotide, consisting either of DNA or of RNA, which codes for a human EAA3 receptor or for a kainate-binding fragment thereof.

In another aspect of the present invention, there is provided a cell that has been genetically engineered to produce a kainate-binding, human EAA receptor belonging to the herein-defined EAA3 family. In related aspects of the present invention, there are provided recombinant DNA constructs and relevant methods useful to create such cells.

In another aspect of the present invention, there is provided a method for evaluating interaction between a test ligand with a genetically engineered cell of the present invention, or with a membrane preparation derived therefrom, and then assessing said interaction by determining receptor/ligand binding.

Other aspects of the present invention, which encompass various applications of the discoveries herein described, will become apparent from the following detailed description, and from the accompanying drawings, in which:

BRIEF REFERENCE TO THE DRAWINGS

FIGS. 1A–1J provide the nucleotide sequence (SEQ ID NO:1) of a cDNA insert comprising DNA coding for an excitatory amino acid receptor of the present invention, and the deduced amino acid sequence (SEQ ID NO:2) thereof;

FIG. 4A shows the differences in the amino acid and nucleic acid sequences of the EAA3b receptor and the EAA3a receptor of FIGS. 1A–1J. The amino acid sequences of human EAAb and human EAAa and the nucleic acid sequences of human EAAb and human EAAa shown in this figure are referred to herein as, respectively, SEQ ID NOs: 3, 4, 5 and 6.

FIG. 4B shows the differences in the amino acid and nucleic acid sequences of the EAA3c receptor and the EAA3a receptor of FIGS. 1A–1J. The amino acid sequences of human EAAc and human EAAa and the nucleic acid sequences of human EAAc and human EAAa shown in this figure are referred to herein as, respectively, SEQ ID NOs: 7, 8, 9 and 10.

FIG. 4C shows the differences in the amino acid and nucleic acid sequences of the EAA3d receptor and the EAA3a receptor of FIGS. 1A–1J. The amino acid sequences of human EAAd and human EAAa and the nucleic acid sequences of human EAAd and human EAAa shown in this figure are listed herein as, respectively, SEQ ID NOs: 11, 12, 13 and 14.

FIG. 5 illustrates the ligand-binding property of an EAA receptor expressed from the coding region provided in FIGS. 1A–1J.

DETAILED DESCRIPTION OF THE INVENTION AND ITS PREFERRED EMBODIMENTS

Figure 2:
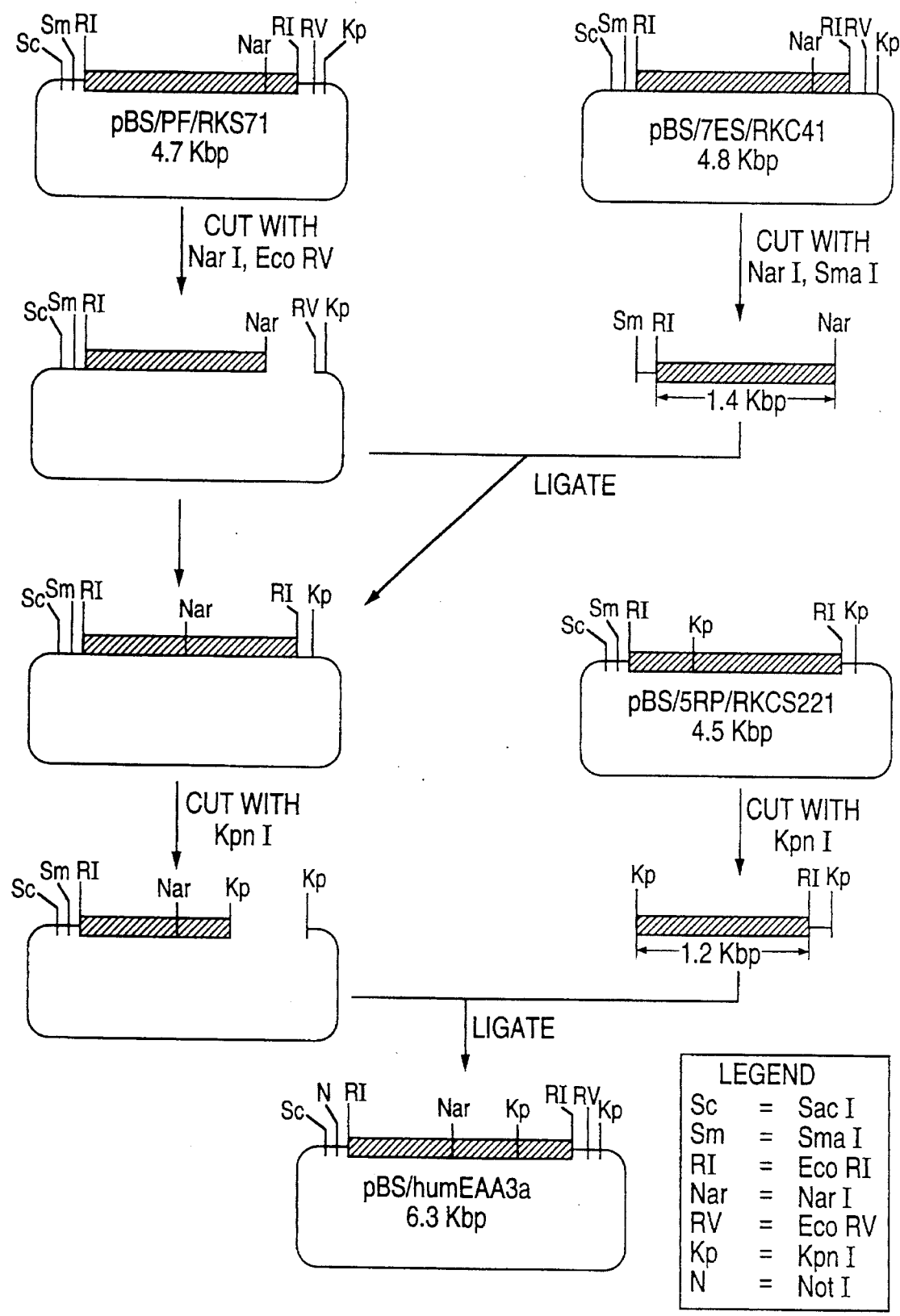
FIG. 2 illustrates with plasmid maps the strategy used to construct a vector harbouring the full-length DNA sequence illustrated in FIGS. 1A–1J.

The invention relates to excitatory amino acid (EAA) receptors of human origin, and is directed more particularly to a novel family of kainate-type human EAA receptors, herein designated the human EAA3 receptor family. As used herein, the term "human EAA3 receptor" is intended to embrace the human EAA3a receptor, and kainate-binding variants of the EAA3a receptor that are structurally related thereto, i.e. share at least 97% amino acid identity including naturally occurring and synthetically derived variants of the EAA3a receptor. Naturally occurring variants of the human EAA3a receptor include particularly the receptors herein designated EAA3b, EAA3c and EAA3d. Synthetically derived variants of the human EAA3a receptor include kainate-binding variants that incorporate one or more, e.g. 1–56, amino acid deletions or additions relative to the EAA3a receptor, or one or more amino acid substitutions, e.g. 1–32 amino acid substitutions relative to the EAA3a receptor.

The term "kainate-binding", as it is used herein with respect to EAA3 receptors, and variants and fragments thereof, is meant to encompass those receptors, variants and fragments that display greater binding affinity for kainate than for either glutamate, AMPA or NMDA, as determined in assays of conventional design, such as the assays herein described.

Each of the naturally occurring members of the EAA3 receptor family possesses structural features characteristic of EAA receptors in general, including extracellular amino (N–) and carboxy-terminal (C-terminal) regions, as well as four internal hydrophobic domains which serve to anchor the receptor within the cell surface membrane. The particular human EAA receptor designated EAA3a is a protein characterized structurally as a single polypeptide chain that is produced initially in precursor form bearing a 30 residue N-terminal signal peptide, and is transported to the cell surface in mature form i.e. lacking the signal peptide and consisting of 875 amino acids arranged in the sequence illustrated, by single letter code, in FIGS. 1A–1J (SEQ ID NO: 2). Unless otherwise stated, the term "EAA3 receptor" refers to the mature form of the receptor protein, and amino acid residues of EAA3 receptors are accordingly numbered with reference to the mature protein sequence. With respect to structural domains of the receptor, hydropathy analysis reveals four putative transmembrane domains, one spanning residues 553–552 inclusive (TM-1), another spanning residues 574–594 (TM-2), a third spanning residues 605–623 (TM-3) and the fourth spanning residues 790–810 (TM-4). Based on this assignment, it is likely that the human EAA3a receptor structure, in its natural membrane-bound form, consists of a 532 amino acid N-terminal extracellular domain, followed by a hydrophobic region containing the four transmembrane domains and an extracellular, 65 amino acid C-terminal domain.

As shown in FIGS. 4A–4C (and in SEQ ID NOS: 3–14) three structurally related variants of the EAA3a receptor, which occur naturally in human brain tissue, have also been identified and are herein designated the EAA3b, EAA3c and EAA3d receptors. As deduced from nucleotide sequences of the genes coding for them, the EAA3b variant shares greater than 99% amino acid identity with EAA3a, differing only by a single amino acid at position 639 which is an aspartate residue in the EAA3a receptor and an asparagine residue in the EAA3b receptor (FIG. 4A) SEQ ID NOS: 3–6. The EAA3c receptor (SEQ ID NO: 1), on the other hand, is a truncated version of EAA3a in which 40 amino acids have been eliminated from the C-terminus. Additionally, the last eleven amino acid residues at the C-terminus of EAA3c, i.e. amino acids at positions 826 to 836, differ from those in the corresponding region of EAA3a as shown in FIG. 4B. (SEQ ID NOS 7–10) In comparison to EAA3a, the EAA3d receptor SEQ ID NO: 1B has a 56 amino acid deletion at its N-terminal end, i.e. the amino acids at positions 6 to 61 in EAA3a are deleted from EAA3d (FIG. 4C) (SEQ ID NOS. 11–14).

Like other members of the human EAA3 receptor family, EAA3a is characterized by a pharmacological profile i.e. a ligand binding "signature", that points strongly to a kainate-type pharmacology, as distinct from other excitatory amino acid receptor types, such as NMDA and AMPA. In addition, and despite the understanding that kainate binding receptors require a multi- and perhaps heteromeric subunit structure to function in the pharmacological sense, it has been found that cells producing the unitary EAA3a receptor do, independently of association with other receptor subunits, provide a reliable indication of excitatory amino acid binding. Thus, in a key aspect of the present invention, the human EAA3a receptor is exploited for the purpose of screening candidate compounds for the ability to interact with the present receptors and/or the ability to compete with endogenous EAA receptor ligands and known synthetic analogues thereof, for EAA receptor interaction.

For use in assessing interaction between the receptor and test ligand, it is desirable to construct by application of genetic engineering techniques a mammalian cell that produces a human EAA3 receptor in functional form as a heterologous product. The construction of such cell lines is achieved by introducing into a selected host cell a recombinant DNA construct in which DNA coding for a secretable form of the human EAA3 receptor, i.e., a form bearing either its native signal peptide or a functional, heterologous equivalent thereof, is associated with expression controlling elements that are functional in the selected host to drive expression of the receptor-encoding DNA, and thus elaborate the desired EAA3 receptor protein. Such cells are herein characterized as having the receptor-encoding DNA incorporated "expressibly" therein. The receptor-encoding DNA is referred to a "heterologous" with respect to the particular cellular host if such DNA is not naturally found in the particular host.

It is most desirable to use a mammalian cell host to produce EAA3 receptors due to the mammalian origin of the present human EAA3 receptors; however, other suitably engineered eukaryotic and prokaryotic hosts may also be employed to produce EAA3 receptors. Accordingly, bacterial hosts such as *E. coli* and *B. subtilis*, fungal hosts such as Aspergillus and yeast and insect cell hosts such as *Spodoptera frugiperda*, are examples of non-mammalian hosts that may also be used to produce EAA3 receptors of the present invention.

The particular cell type selected to serve as host for production of the human EAA3 receptor can be any of several cell types currently available in the art, but should not of course be a cell type that in its natural state elaborates a surface receptor that can bind excitatory amino acids, and so confuse the assay results sought from the engineered cell line. Generally, such problems are avoided by selecting as host a non-neuronal cell type, and can further be avoided using non-human cell lines, as is conventional. It will be appreciated that neuronal- and human- type cells may nevertheless serve as expression hosts, provided that "background" binding to the test ligand is accounted for in the assay results.

According to one embodiment of the present invention, the cell line selected to serve as host for EAA3 receptor production is a mammalian cell. Several types of such cell lines are currently available for genetic engineering work, and these include the chinese hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells; human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with these hosts and are now commercially available, and any one of these systems can be exploited to drive expression of the EAA3 receptor-encoding DNA. These systems, available typically in the form of plasmidic vectors, incorporate expression cassettes the functional components of which include DNA constituting expression controlling sequences, which are host-recognized and enable expression of the receptor-encoding DNA when linked 5' thereof. The systems further incorporate DNA sequences which terminate expression when linked 3' of the receptor-encoding region. Thus, for expression in the selected mammalian cell host, there is generated a recombinant DNA expression construct in which DNA coding for a secretable form of the receptor is linked with expression controlling DNA to drive expression, and a 3' region to terminate expression. The plasmidic vector harbouring the expression construct typically incorporates such other functional components as an origin of replication, usually virally-derived, to permit replication of the plasmid in the expression host and desirably also for plasmid amplification in a bacterial host, such as *E. coli*. To provide a marker enabling selection of stably transformed recombinant cells, the vector will also incorporate a gene conferring some survival advantage on the transformants, such as a gene coding for neomycin resistance in which case the transformants are plated in medium supplemented with neomycin.

Included among the various recombinant DNA expression systems that can be used to achieve mammalian cell expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drosophila, as well as mammalian gene promoters such as steroid-inducible promoters and those regulated by heavy metals i.e. the metallothionein gene promoter.

For incorporation into the recombinant DNA expression vector, DNA coding for the desired EAA3 receptor, e.g. the EAA3a receptor or a kainate-binding variant thereof, can be obtained by applying selected techniques of gene isolation or gene synthesis. As described in more detail in the examples herein, the EAA3a receptor, and the EAA3b, EAA3c, and EAA3d variants thereof, are encoded within the genome of human brain tissue, and can therefore be obtained by careful application of conventional gene isolation and cloning techniques. This typically will entail extraction of total messenger RNA from a fresh source of human brain tissue, such as cerebellum or hippocampus tissue and preferably fetal brain tissue, followed by conversion of message to cDNA and formation of a library in for example a bacterial plasmid, more typically a bacteriophage. Such bacteriophage harbouring fragments of the human DNA are typically grown by plating on a lawn of susceptible *E. coli* bacteria, such that individual phage plaques or colonies can be isolated. The DNA carried by the phage colony is then typically immobilized on a nitrocellulose or nylon-based hybridization membrane, and then hybridized, under carefully controlled conditions, to a radioactively (or otherwise) labelled oligonucleotide probe of appropriate sequence to identify the particular phage colony carrying receptor-encoding DNA or fragment thereof. Typically, the gene or a portion thereof so identified is subcloned into a plasmidic vector for nucleic acid sequence analysis.

Having herein provided the nucleotide sequence of various human EAA3 receptors, it will be appreciated that automated techniques of gene synthesis and/or amplification can be performed to generate DNA coding therefor. Because of the length of EAA3 receptor-encoding DNA, application of automated synthesis may require stages gene construction, in which regions of the gene up to about 300 nucleotides in length are synthesized individually and then ligated in correct succession for final assembly. Individually synthesized gene regions can be amplified prior to assembly, using polymerase chain reaction (PCR) technology.

The application of automated gene synthesis techniques provides an opportunity for generating sequence variants of naturally occurring members of the EAA3 gene family. It will be appreciated that polynucelotides coding for the EAA3 receptors herein described can be generated by substituting synonymous codons for those represented in the naturally occurring polynucleotide sequences herein identified. In addition, polynucleotides coding for synthetic variants of the EAA3 receptors herein described can be generated which for example incorporate one or more single amino acid substitutions, deletions or additions. Since it will for the most part be desirable to retain the natural ligand binding profile of the receptor for screening purposes, it is desirable to limit amino acid substitutions, for example to the so-called conservative replacements in which amino acids of like charge are substituted, and to limit substitutions to those sites less critical for receptor activity e.g. within about the first 20 N-terminal residues of the mature receptor, and such other regions as are elucidated upon receptor domain mapping.

With appropriate template DNA in hand, the technique of PCR amplification may also be used to directly generate all or part of the final gene. In this case, primers are synthesized which will prime the PCR amplification of the final product, either in one piece, or in several pieces that may be ligated together. This may be via step-wise ligation of blunt ended, amplified DNA fragments, or preferentially via step-wise ligation of fragments containing naturally occurring restriction endonuclease sites. In this application, it is possible to use either cDNA or genomic DNA as the template for the PCR amplification. In the former case, the cDNA template can be obtained from commercially available or self-constructed cDNA libraries of various human brain tissues, including hippocampus and cerebellum.

Once obtained, the receptor-encoding DNA is incorporated for expression into any suitable expression vector, and host cells are transfected therewith using conventional procedures, such as DNA-mediated transformation, electroporation, microinjection, or particle gun transformation. Expression vectors may be selected to provide transformed cell lines that express the receptor-encoding DNA either transiently or in a stable manner. For transient expression, host cells are typically transformed with an expression vector harbouring an origin of replication functional in a mammalian cell. For stable expression, such replication origins are unnecessary, but the vectors will typically harbour a gene coding for a product that confers on the transformants a survival advantage, to enable their selection. Genes coding for such selectable markers including the *E. coli* gpt gene which confers resistance to mycophenolic acid, the neo gene from transposon Tn5 which confers resistance to the antibiotic G418 and to neomycin, the dhfr sequence from murine cells or *E. coli* which changes the phenotype of DHFR-cells into DHFR+cells, and the tk gene of herpes simplex virus, which makes TK-cells phenotypically TK+cells. Both transient expression and stable expression can provide transformed cell lines, and membrane preparations derived therefrom, for use in ligand screening assays.

For use in screening assays, cells transiently expressing the receptor-encoding DNA can be stored frozen for later use, but because the rapid rate of plasmid replication will lead ultimately to cell death, usually in a few days, the transformed cells should be used as soon as possible. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purposes, i.e., ligand binding experiments, frozen intact cells are homogenized while in cold water suspension and a membrane pellet is collected after centriguation. The pellet is then washed in cold water, and dialyzed to remove endogenous EAA ligands such as glutamate, that would otherwise compete for binding in the assays. The dialyzed membranes may then be used as such, or after storage in lyophilized form, in the ligand binding assays. Alternatively, intact, fresh cells harvested about two days after transient transfection or after about the same period following fresh plating of stably transfected cells, can be used for ligand binding assays by the same methods as used for membrane preparations. When cells are used, the cells must be harvested by more gentle centrifugation so as not to damage them, and all washing must be done in a buffered medium, for example in phosphate-buffered saline, to avoid osmotic shock and rupture of the cells.

The EAA3 receptors of the present invention are per se functional in an electrophysiological context, and are therefore useful, in the established manner, in screening test ligands for their ability to modulate ion channel activity. The present invention thus further provides, as a ligand screening technique, a method of detecting interaction between a test ligand and a human CNS receptor, which comprises the steps of incubating the test ligand with a human EAA3 receptor-producing cell or with a membrane preparation derived therefrom, and then measuring ligand-induced electrical current across said cell or membrane.

As an alternative to using cells that express receptor-encoding DNA, ligand characterization may also be performed using cells, for example Xenopus oocytes, that yield functional membrane-bound receptor following introduction of messenger RNA coding for the EAA3 receptor. In this case, the EAA3 receptor gene of the invention is typically subcloned into a plasmidic vector such that the introduced gene may be easily transcribed into RNA via an adjacent RNA transcription promoter supplied by the plasmidic vector, for example the T3 or T7 bacteriophage promoters. RNA is then transcribed from the inserted gene in vitro, and can then be injected into Xenopus oocytes. Following the injection of nL volumes of an RNA solution, the oocytes are left to incubate for up to several days, and are then tested in either intact form or as a membrane preparation for the ability to bind a particular ligand molecule supplied in a bathing solution. Since functional EAA receptors act in part by operating a membrane channel through which ions may selectively pass, the functioning of the receptor in response to a particular ligand molecule in the bathing solution may typically be measured as an electrical current utilizing microelectrodes inserted into the cell or placed on either side of a cell-derived membrane preparation using the "patch-clamp" technique.

The binding of a candidate ligand to a selected human EAA3 receptor of the invention is evaluated typically using a predetermined amount of cell-derived membrane (measured for example by protein determination), generally from about 25 ug to 100 ug. Generally, competitive binding assays will be useful to evaluate the affinity of a test compound relative to kainate. This competitive binding assay can be performed by incubating the membrane preparation with radiolabelled kainate, for example [3H]-kainate, in the presence of unlabelled test compound added at varying concentrations. Following incubation, either displaced or bound radiolabelled kainate can be recovered and measured, to determine the relative binding affinities of the test compound and kainate for the particular receptor used as substrate. In this way, the affinities of various compounds for the kainate-type human EAA receptors can be measured.

In addition to using the receptor-encoding DNA to construct cell lines useful for ligand screening, expression of the DNA can, according to another aspect of the invention, be performed to produce fragments of the receptor in soluble form, for structure investigation, to raise antibodies and for other experimental uses. It is expected that kainate-binding fragments, i.e., the portion of the EAA3 receptor responsible for binding a ligand molecule, resides on the outside of the cell, i.e., is extracellular. It is therefore desirable in the first instance to facilitate the characterization of the receptor-ligand interaction by providing such kainate binding fragments in quantity and in isolated form, i.e., free from the remainder of the receptor. To accomplish this, the full-length EAA3 receptor-encoding DNA may be modified by site-directed mutagenesis, to introduce a translational stop codon into the extracellular N-terminal region, immediately 5' of the first transmembrane domain (TM1), i.e., before the residue 533 codon as shown in FIGS. 1A–1J. (SEQ ID NO: 1) Since there will no longer be produced any transmembrane domain(s) to "anchor" the receptor into the membrane, expression of the modified gene will result in the secretion, in soluble form, of only the extracellular ligand-binding domain. Standard ligand-binding assays may then be performed to ascertain the degree of binding of a candidate compound to the extracellular domain so produced. It may of course be necessary, using site-directed mutagenesis, to produce different versions of the extracellular regions, in order to map the ligand binding domain with precision. It will also be appreciated that the length of the fragment may be varied, i.e. to lengths less than the entire 533 amino acid extracellular N-terminal domain.

Alternatively, it may be desirable to produce an extracellular domain of the receptor which is not derived from the N-terminus of the mature protein, but rather from the C-terminus, for example domains immediately following the fourth transmembrane domain (TM4), i.e., residing between amino acid residues 811 and 875 inclusive as shown in FIGS. 1A–1J. (SEQ ID NO: 1) In this case, site-directed mutagenesis and/or PCR-based amplification techniques may readily be used to provide a defined fragment of the gene encoding the receptor domain of interest. Direct peptide synthesis may also be used to make the desired C-terminal fragment, or as noted above, desired N-terminal fragments. Such a DNA sequence may be used to direct the expression of the desired N-terminal fragments, either intracellularly, or in secreted fashion, provided that the DNA encoding the gene fragment is inserted adjacent to a translation start codon provided by the expression vector, and that the required translation reading frame is carefully conserved.

It will be appreciated that the production of such extracellular ligand binding domains may be accomplished in a variety of host cells. Mammalian cells such as CHO cells may be used for this purpose, the expression typically being driven by an expression promoter capable of high-level expression, for example the CMV (cytomegalovirus) promoter. Alternately, non-mammalian cells, such as insect Sf9 (*Spodoptera frugiperda*) cells may be used, with the expression typically being driven by expression promoters of the baculovirus, for example the strong, late polyhedrin protein promoter. Filamentous fungal expression systems may also be used to secrete large quantities of such extracellular domains of the EAA receptor. *Aspergillus nidulans*, for example, with the expression being driven by the alcA promoter, would constitute such as acceptable system. In addition to such expression hosts, it will be further appreciated that any prokaryotic or other eukaryotic expression system capable of expressing heterologous genes or gene fragments, whether intracellularly or extracellularly would be similarly acceptable.

For use particularly in detecting the presence and/or location of an EAA3 receptor, for example in brain tissue, the present invention also provides, in another of its aspects, labelled antibody to a human EAA3 receptor. To raise such antibodies, there may be used as immunogen either the intact, soluble receptor or an immunogenic fragment thereof, produced in a microbial or mammalian cell host as described above or by standard peptide synthesis techniques. Regions of the EAA3a receptor particularly suitable for use as immunogenic fragments include those corresponding in sequence to an extracellular region of the receptor, or a portion of the extracellular region, such as peptides consisting of residues 1–532 or fragments thereof, including particularly residues 186–201 or 485–528, and peptides corresponding to the region between transmembrane domains TM-2 and TM-3, such as a peptide consisting of residues 595–604. Peptides consisting of the C-terminal domain (residues 811–875), or fragments thereof may also be used for the raising of antibodies. Substantially the same region of the human EAA3b, EAA3c and EAA3d receptor may also be used for production of antibodies against this receptor.

The raising of antibodies to the desired EAA3 receptor or immunogenic fragment can be achieved, for polyclonal antibody production, using immunization protocols of conventional design, and any of a variety of mammalian hosts, such as sheep, goats and rabbits. Alternatively, for monoclonal antibody production, immunocytes such as splenocytes can be recovered from the immunized animal and fused, using hybridoma technology, to myeloma cells. The fusion products, i.e. hybridomas, are then screened by culturing in a selection medium, and cells producing antibody are recovered for continuous growth, and antibody recovery. Recovered antibody can then be coupled covalently to a reported molecule, i.e. a detectable label such as a radiolable, enzyme label, luminescent label or the like, using linker technology established for this purpose, to form a specific probe for EAA3 receptors.

In detectably labelled form, e.g. radiolabelled form, DNA or RNA coding for the human EAA3 receptor, and selected regions thereof, may also be used, in accordance with another aspect of the present invention, as hybridization probes for example to identify sequence-related genes resident in the human or other mammalian genomes (or cDNA libraries) or to locate the EAA3-encoding DNA in a specimen, such as brain tissue. This can be done using either the intact coding region, or a fragment thereof having radiolabelled e.g. $^{32}$P, nucleotides incorporated therein. To identify the EAA3-encoding DNA in a specimen, it is desirable to use either the full length cDNA coding therefor, or a fragment which is unique thereto. With reference to FIGS. 1A–1J (SEQ ID NO: 1) and the nucleotide numbering appearing thereon, such nucleotide fragments include those comprising at least about 17 nucleic acids, and otherwise corresponding in sequence to a region coding for the N-terminus or C-terminus of the receptor, or representing a 5'-untranslated or 3'-untranslated region thereof. Examples of suitable nucleotide fragments for this purpose include nucleotides 426–446 and nucleotides 1251–1271 of EAA3a. These sequences, among others, as well as the intact gene itself, may also be used of course to clone EAA3-related human genes, particularly cDNA equivalents thereof, by standard hybridization techniques.

Embodiments of the present invention are described in detail in the following non-limiting Examples.

EXAMPLE 1

Isolation of DNA Coding for the Human EAA3a Receptor cDNA coding for the human EAA3a receptor was identified by probing human fetal brain cDNA that was obtained as an EcoRI-based lambda phage library (lambda ZAP) from Stratagene Cloning Systems (La Jolla, Calif., U.S.A.). The cDNA library was screened using an oligonucleotide probe having the following specific sequence: (SEQ ID NO: 5)

5'-ATCGGCGGCATCTTCATTGTTCTGGCTG-CAGGACTCGTGC-3'

The fetal brain cDNA library was screened under the following hybridization conditions; 6×SSC, 25% formamide, 5×Denhardt's solution, 10 mM Na$_2$HPO$_4$ buffer, 0.5% sodium pyrophosphate, 0.5% SDS, 100 µg/ml denatured salmon sperm DNA, 42° C. Filters were washed with 6×SSC containing 0.5% SDS at 25° C. for 5 minutes, followed by a 15 minute wash at 42° C. with 2×SSC containing 0.5% SDS. The final wash was with 1×SSC containing 0.5% SDS at 50° C. for 15 minutes. Filters were exposed to X-ray film (Kodak) overnight. Of 10$^6$ clones screened, only two cDNA inserts were identified; one of about 0.9 kb designated RKCSFG72, and another of about 2.7 kb designated RKCS5F81. For sequencing, the '72 and '81 phages were plaque purified, then excised as phagemids according to the supplier's specifications, to generate insert-carrying Bluescript-SK variants of the phagemid vectors. Sequencing of the '72 clone across its entire sequence revealed an open reading frame representing the C-terminal region but no putative termination codon. Sequencing across the '81 insert revealed a DNA sequence with about 80% identity with the '72 clone. The '81 clone displayed significant overlap to the '72 clone and included an additional 5' sequence.

Since no initiation and termination codons were apparent in the '72 sequence, the 5' and 3' regions of the '72 clone was sought. For this purpose, a 2.0 kb EcoRI fragment representing the '81 clone and a 0.9 kb EcoRI fragment representing the '72 clone were isolated, $^{32}$P-labelled, and then used to re-screen the same fetal brain cDNA library under the following hybridization conditions: 6×SSC, 25% formamide, 5×Denhardt's solution, 0.5% SDS, 100 µg/ml denatured salmon sperm DNA, 30° D. Filters were washed twice with 2×SSC containing 0.5% SDS at 25° C. for 5 minutes, followed by a 15 minute final wash at 42° C. with 2×SSC containing 0.5% SDS. Filters were exposed to X-ray film (Kodak) overnight. Of 10$^6$ clones screened, only two cDNA were identified, one of about 1.5 kb designated RKCS221, and the another of about 1.8 kb designated RKC41. Sequencing the entire '221 insert revealed more of the 5' sequence of the '72 clone as well as a termination codon and about 250 bases of the 3' non-coding region. Sequencing the entire '41 insert revealed more of the 5' sequence but still did not reveal an initiation codon.

Thus, the same fetal brain cDNA library was screened using an oligonucleotide probe (based on the '41 sequence) capable of annealing to the 5' region of the '41 sequence. The specific sequence (SEQ ID NO: 16) of the 32P-labelled probe is provided below:

5'-CCATCATTGAGAAGTGGTCC-3'

This probe was $^{32}$P-labelled and then used to re-screen the same fetal brain cDNA library under the following hybridization conditions: 6×SSC, 50% formamide, 5×Denhardt's solution, 0.5% SDS, 100 µg/ml denatured salmon sperm DNA, 30° C. Filters were washed twice with 2×SSC containing 0.5% SDS at 25° C. for 5 minutes, followed by a 15 minute final wash at 42 ° C. with 2×SSC containing 0.5% SDS. Filters were exposed to X-ray film (Kodak) overnight. Of 10$^6$ clones screened, a single cDNA insert was identified of about 1.7 kb designated RKS71. The '71 insert, when sequence, revealed the initiation codon together with about 417 bases of 5' non-coding region and a significant overlap with the '41 insert.

To provide the entire coding region of the receptor, the strategy depicted in FIG. 2 was then applied to generate the 6.3 kb phagemid pBS/humEEA3a which carries the intact EAA3a receptor-encoding DNA as a 3.3 kb NotI/HindIII insert in a 3.0 kb pBluescript phagemid background. Phagemid pBS/humEAA3a was deposited under the terms of the Budapest Treaty with the American Type Culture Collection in Rockville, Md. USA on Nov. 12, 1992, and has been assigned accession number ATCC 75350.

EXAMPLE 2

Figure 3:
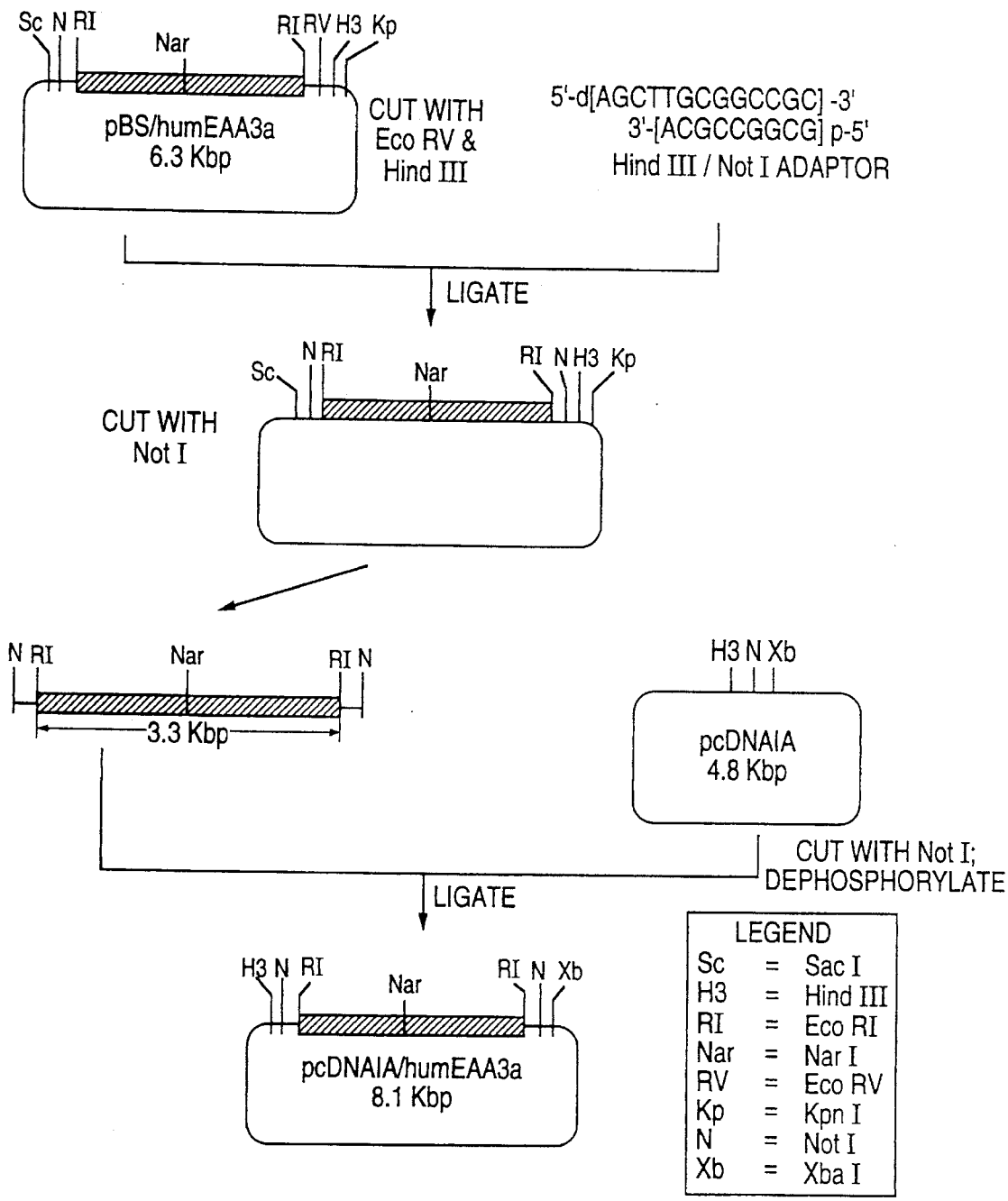
FIG. 3 illustrates with plasmid maps the strategy used to construct expression vectors harbouring the DNA sequence illustrated in FIGS. 1A–1J.

Construction of Genetically Engineered Cells Producing the Human EAA3a Receptor For transient expression in mammalian cells, cDNA encoding the EAA3a receptor was incorporated into the mammalian expression vector pcDNAI/Amp (pcDNAIA), which is available commercially from Invitrogen Corporation (San Diego, Calif., USA; catalogue number V490-20), as depicted in FIG. 3. pcDNAIA is a multifunctional 4.8 kb plasmid vector designed for cDNA expression in eukaryotic systems, and cDNA analysis in prokaryotes. Incorporated on the vector are the CMV promoter and enhancer, splice segment and polyadenylation signal, an SV40 and Polyoma virus origin of replication, M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter and 3' of the T7 promoter.

Briefly, the EAA3a-encoding cDNA insert was released from pBS/humEAA3a as a 3.3 kb NotI/NotI fragment subsequent to insertion of a HindIII/NotI adaptor at the 3' end of the insert. The 3.3 kb fragment was then incorporated at the NotI site in the pcDNAIA vector to form the expression vector pcDNAIA/humEAA3a.

For transient expression of the EAA3a-encoding DNA, monkey-derived, fibroblast-like cells of the COS-1 lineage (available from the American Type Culture Collection, Rockville, Md as ATCC CRL 1650) were transfected with approximately 8 ng DNA (as pcDNAIA/humEAA3a) per $10^6$ COS cells, by DEAE-mediated DNA transfection and treated with chloroquine according to conventional procedures. Briefly, COS-1 cells were plated at a density of $5 \times 10^6$ cells/dish and then grown for 24 hours in FBS-supplemented DMEM/F12 medium. Medium was then removed and cells were washed with PBS and then with medium. There was then applied on the cells 10 ml of a transfection solution containing DEAE dextran (0.4 mg/ml), 100 μM chloroquine, 10% NuSerum, DNA (0.4 ng/ml) in DMEM/F12 medium. After incubation for 3 hours at 37° C., cells were washed in PBS and medium. Cells were allowed and then shocked for 1 minute with 10% DMSO in DMEM/F12 medium. Cells were allowed to grow for 2–3 days in 10% FBS-supplemented medium, and at the end of incubation dishes were placed on ice, the cells were washed with ice cold PBS and then removed by scraping. Cells were then harvested by centrifugation at 1000 rpm for 10 minutes at the cellular pellet was frozen in liquid nitrogen, for subsequent use in ligand binding assays. Northern blot analysis of a thawed aliquot of frozen cells confirmed expression of receptor-encoding cDNA in cells under storage.

In a like manner, stably transfected cell lines can also be prepared using two different cell types as host: CHO K1 and CHO Pro5. To construct these cell lines, cDNA coding for human EAA3a is incorporated into the mammalian expression vector pRC/CMV (Invitrogen), which enables stable expression. Insertion at this site places the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

To introduce plasmids constructed as described above, the host CHO cells are first seeded at a density of $5 \times 10^5$ in 10% FBS-supplemented αMEM medium. After growth for 24 hours, fresh medium is added to the plates and three hours later, the cells are transfected using the conventional calcium phosphate-DNA co-precipitation procedure. Briefly, 3 μg of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/ml). Individual colonies of G418-resistant cells are isolated about 2–3 weeks later, clonally selected and then propogated for assay purposes.

EXAMPLE 3

Ligand Binding Assays

Transfected cells in the frozen state were resuspended in ice-cold distilled water using a hand homogenizer and centrifuged for 20 minutes at 50,000 g. The supernatant was discarded and the membrane pellet stored frozen at −71° C.

COS cell membrane pellets were suspended in ice cold 50 mM Tris-Hcl (pH 7.55 5° C.) and centrifuged again at 50,000 g for 10 minutes in order to remove endogenous glutamate that would compete for binding. Pellets were resuspended in ice cold 50 mM Tris-Hcl (pH 7.55) buffer and the resultant membrane preparation was used as tissue source for binding experiments described below. Proteins were determined using the Pierce Reagent with BSA as standard.

Binding assays were then performed, using an amount of COS-derived membrane equivalent to 25–100 ug as judged by protein determination and selected radiolabelled ligand. In particular, for kainate binding assays, incubation mixtures consisted of 25–100 μg tissue protein and [vinylidene-3H] kainic acid (58 Ci/mmole, 80 nM final) in the cold incubation buffer, 1 ml final volume. Non-specific binding was in the presence of 1 mM L-glutamate. Samples were incubated on ice for 60 minutes, and bound and free ligand were then separated by rapid filtration using a PHD cell harvester and GF/B filters pre-soaked in ice-cold 0.3% polyethyleneimine. Filters were washed twice in 4 ml of the cold incubation buffer, then placed in scintillation vials with 5 ml of Beckman Ready-Protein Plus scintillation cocktail for counting.

For AMPA-binding assays, incubation mixtures consisted of 25–100 ug tissue protein and D,L-α-[5-methyl-3H] amino-3-hydroxy-5-methylisoxazole-4-propionic acid (3H-AMPA, 27.6 Ci/mmole, 10 nM final) with 0.1M KSCN and 2.5 mM $CaCl_2$ in the 1 ml final volume. Non-specific binding was determined in the presence of 1 mM L-glutamate. Samples were incubated on ice for 60 minutes in plastic minivials, and bound and free ligand were separated by centrifugation for 30 minutes at 50,000 g. Pellets were washed twice in 4 ml of the cold incubation buffer, then 5 ml of Beckman Ready-Protein Plus scintillation cocktail was added, for counting.

Assays performed in this manner, using membrane preparations derived from the EAA3a-producing COS cells, revealed specific [3H]-kainate binding of 167 fmol/mg protein at 80 nM, labelled ligand (FIG. 4). Mock transfected cells exhibited no specific binding of any of the ligands tested. These results demonstrate clearly that the human EAA3a receptor is binding kainate specifically. This activity, coupled with the fact that there is little or no demonstrable binding of either AMPA or NMDA clearly assigns the EAA3a receptor to be of the kainate type of EAA receptor. Furthermore, this binding profile indicates that the receptor is functioning in an authentic manner, and can therefore reliably predict the ligand "signature" of its non-recombinant counterpart from the intact human brain. These features make the recombinant receptor especially useful for selecting and characterizing ligand compounds which bind to the receptor, and/or for selecting and characterizing compounds which may act by displacing other ligands from the receptor. The isolation of the EAA3a receptor gene in a pure form, capable of being expressed as a single, homogenous receptor species, therefore frees the ligand binding assay from the lack of precision introduced when complex, heterogeneous receptor preparations from human and non-human brains are used to attempt such characterizations.

We claim:

1. An isolated and purified polynucleotide that codes for a kainate-binding human EAA3 receptor selected from the group consisting of: a human EAA3c receptor having the amino acid sequence of residues 1–836 of SEQ ID NO: 17, a human EAA3c receptor having the amino acid sequence of SEQ ID NO: 17, a human EAA3d receptor having the amino acid sequence of residues 31–848 of SEQ ID NO: 18 and a human EAA3d receptor having the amino acid sequence of SEQ ID NO: 18.

2. An isolated polynucleotide according to claim 1, consisting of DNA.

3. An isolated polynucleotide according to claim 2, that codes for a human EAA3c receptor selected from the group consisting of a human EAA3c receptor having the amino acid sequence of residues 1–836 of SEQ ID NO: 17 and a human EAA3c receptor having the amino acid sequence of SEQ ID NO: 17.

4. An isolated polynucleotide according to claim 2, that codes for a human EAA3d receptor selected from the group consisting of a human EAA3d receptor having the amino acid sequence of residues 31–848 of SEQ ID NO: 18 and a human EAA3d receptor having the amino acid sequence of SEQ ID NO: 18.

5. A recombinant DNA construct having incorporated therein a polynucleotide as defined in claim 2.

6. A process for obtaining a substantially homogenous source of a human EAAc or EAA3d receptor, which comprises the steps of culturing cells having incorporated expressibly therein a polynucleotide as defined in claim 2 encoding a human EAA3c or EAA3d receptor, and then recovering the cultured cells.

7. A process for obtaining a substantially homogeneous source of a human EAA3c or EAA3d receptor according to claim 6, comprising the subsequent step of obtaining a membrane preparation containing said receptor from the cultured cells.

8. A transformed cell having incorporated expressibly therein a heterologous polynucleotide as defined in claim 1, whereby said cell produces said EAA3c or said EAA3d receptor.

9. A cell as defined in claim 8, which is a mammalian cell.

10. A cell as defined in claim 8, which is an amphibian oocyte.

11. A cell according to claim 8, wherein said heterologous polynucleotide codes for a human EAA3c receptor selected from the group consisting of a human EAA3c receptor having the amino acid sequence of residues 1–836 of SEQ ID NO: 17 and a human EAA3c receptor having the amino acid sequence of SEQ ID NO: 17.

12. A cell as defined in claim 11, wherein said cell is a mammalian cell.

13. A cell as defined in claim 11, wherein said cell is an amphibian oocyte.

14. A cell according to claim 8, wherein said heterologous polynucleotide codes for a human EAA3d receptor, wherein said receptor has an amino acid sequence selected from the group consisting of the amino acid sequence of residues 31–848 of SEQ ID NO: 18 and the amino acid sequence of SEQ ID NO: 18.

15. A cell as defined in claim 14, wherein said cell is a mammalian cell.

16. A cell as defined in claim 14, wherein said cell is an amphibian oocyte.

17. A membrane-containing preparation derived from a cell as defined in claim 8, wherein said preparation comprises said human EAA3c or human EAA3d receptor.

18. A membrane-containing preparation derived from a cell as defined in claim 11, wherein said preparation comprises said human EAA3c receptor.

19. A membrane-containing preparation derived from a cell as defined in claim 12, wherein said preparation comprises said human EAA3c receptor.

20. A membrane-containing preparation derived from a cell as defined in claim 14, wherein said preparation comprises said human EAA3d receptor.

21. A membrane-containing preparation derived from a cell as defined in claim 15, wherein said preparation comprises said human EAA3d receptor.

22. A human EAA3 receptor protein in a form essentially free from other proteins of human origin, wherein said receptor protein has an amino acid sequence selected from the group consisting of: the EAA3c amino acid sequence of residues 1–836 of SEQ ID NO: 17, the EAA3c amino acid sequence of SEQ ID NO: 17, the EAA3d amino acid sequence of residues 31–848 of SEQ ID NO: 18, and the EAA3d amino acid sequence of SEQ ID NO: 18.

23. A receptor protein according to claim 22 which has the amino acid sequence of EAA3c selected from the group consisting of the amino acid sequence of residues 1–836 of SEQ ID NO: 17 and the amino acid sequence of SEQ ID NO: 17.

24. A receptor protein according to claim 22 which has the amino acid sequence of EAA3d selected from the group consisting of the amino acid sequence of residues 31–848 of SEQ ID NO: 18 and the amino acid sequence of SEQ ID NO: 18.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 3385 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 418..3132

( i x ) FEATURE:
( A ) NAME/KEY: mat_peptide
( B ) LOCATION: 508..3132

( i x ) FEATURE:
( A ) NAME/KEY: sig_peptide
( B ) LOCATION: 418..507

( x i ) SEQUENCE DESCRIPTION: SEQ ID NO:1:

```
GAATTCCGTC TTCTTTCCCC CTTTTCCCTC CTCTGTCTGT GCCTATCCCC CGACTTTTGC    60

ATCTGACCAA AGGACGAATG AGGGAGACGT TCCTGCAGAT CGGGGCAGCA ACTTTCCTCA   120

GCTGGTCTCT GGGCTCCGGA GCCAGAGAGC GCTGATCCTC CGCGTCTGCG GCCCATGAAG   180

AGAGAGAGAG CCGTGATGGG CTAGCGACAG CACTGAGGAG CCCCGAGAGA GCTCAGCCTT   240

GCCAGCCAGC TCCGCGGTCC CACGCGGGTT CCCTCGAGCT CGCTCCGTGG GGAGCGCGCA   300

GCGTGCTTGG AACCGGAGCA TCCAGAGAGG ATGAGGCGGG GACCCGGCCC AAGTTGGGTG   360

CATCTCTCGG GCGTCCGGCA GCGGCTGTAT CTCGGCATGA ATTAAGAAGC TAGGAAG      417
```

| ATG | GAG | CAC | GGC | ACA | CTC | CTC | GCC | CAG | CCC | GGG | CTC | TGG | ACC | AGG | GAC | 465 |
|-----|-----|-----|-----|-----|-----|-----|-----|-----|-----|-----|-----|-----|-----|-----|-----|-----|
| Met | Glu | His | Gly | Thr | Leu | Leu | Ala | Gln | Pro | Gly | Leu | Trp | Thr | Arg | Asp | |
| -30 | | | | -25 | | | | | -20 | | | | | | -15 | |

| ACC | AGC | TGG | GCA | CTC | CTC | TAT | TTC | CTC | TGC | TAT | ATC | CTC | CCT | CAG | ACC | 513 |
|-----|-----|-----|-----|-----|-----|-----|-----|-----|-----|-----|-----|-----|-----|-----|-----|-----|
| Thr | Ser | Trp | Ala | Leu | Leu | Tyr | Phe | Leu | Cys | Tyr | Ile | Leu | Pro | Gln | Thr | |
| | | | | -10 | | | | | -5 | | | | | | 1 | |

| GCC | CCG | CAA | GTA | CTC | AGG | ATC | GGA | GGG | ATT | TTT | GAA | ACA | GTG | GAA | AAT | 561 |
|-----|-----|-----|-----|-----|-----|-----|-----|-----|-----|-----|-----|-----|-----|-----|-----|-----|
| Ala | Pro | Gln | Val | Leu | Arg | Ile | Gly | Gly | Ile | Phe | Glu | Thr | Val | Glu | Asn | |
| | | | 5 | | | | | 10 | | | | | 15 | | | |

| GAG | CCT | GTT | AAT | GTT | GAA | GAA | TTA | GCT | TTC | AAG | TTT | GCA | GTC | ACC | AGC | 609 |
|-----|-----|-----|-----|-----|-----|-----|-----|-----|-----|-----|-----|-----|-----|-----|-----|-----|
| Glu | Pro | Val | Asn | Val | Glu | Glu | Leu | Ala | Phe | Lys | Phe | Ala | Val | Thr | Ser | |
| | 20 | | | | | 25 | | | | | | 30 | | | | |

| ATT | AAC | AGA | AAC | CGA | ACC | CTG | ATG | CCT | AAC | ACC | ACA | TTA | ACC | TAT | GAC | 657 |
|-----|-----|-----|-----|-----|-----|-----|-----|-----|-----|-----|-----|-----|-----|-----|-----|-----|
| Ile | Asn | Arg | Asn | Arg | Thr | Leu | Met | Pro | Asn | Thr | Thr | Leu | Thr | Tyr | Asp | |
| 35 | | | | | 40 | | | | | 45 | | | | | 50 | |

| ATC | CAG | AGA | ATT | AAC | CTT | TTT | GAT | AGT | TTT | GAA | GCC | TCG | CGG | AGA | GCA | 705 |
|-----|-----|-----|-----|-----|-----|-----|-----|-----|-----|-----|-----|-----|-----|-----|-----|-----|
| Ile | Gln | Arg | Ile | Asn | Leu | Phe | Asp | Ser | Phe | Glu | Ala | Ser | Arg | Arg | Ala | |
| | | | | 55 | | | | | 60 | | | | | 65 | | |

| TGT | GAC | CAG | CTG | GCT | CTT | GGT | GTG | GCT | GCT | CTC | TTT | GGC | CCT | TCC | CAT | 753 |
|-----|-----|-----|-----|-----|-----|-----|-----|-----|-----|-----|-----|-----|-----|-----|-----|-----|
| Cys | Asp | Gln | Leu | Ala | Leu | Gly | Val | Ala | Ala | Leu | Phe | Gly | Pro | Ser | His | |
| | | | 70 | | | | | 75 | | | | | 80 | | | |

| AGC | TCC | TCC | GTC | AGT | GCT | GTG | CAG | TCT | ATT | TGC | AAT | GCT | CTC | GAA | GTT | 801 |
|-----|-----|-----|-----|-----|-----|-----|-----|-----|-----|-----|-----|-----|-----|-----|-----|-----|
| Ser | Ser | Ser | Val | Ser | Ala | Val | Gln | Ser | Ile | Cys | Asn | Ala | Leu | Glu | Val | |
| | | 85 | | | | | 90 | | | | | 95 | | | | |

| CCA | CAC | ATA | CAG | ACC | CGC | TGG | AAA | CAC | CCC | TCG | GTG | GAC | AAC | AAA | GAT | 849 |
|-----|-----|-----|-----|-----|-----|-----|-----|-----|-----|-----|-----|-----|-----|-----|-----|-----|
| Pro | His | Ile | Gln | Thr | Arg | Trp | Lys | His | Pro | Ser | Val | Asp | Asn | Lys | Asp | |

|  |  |  |  |  |  |  |  |  |  |  |  |  |  |  |  |
|---|---|---|---|---|---|---|---|---|---|---|---|---|---|---|---|
|  | 100 |  |  |  |  | 105 |  |  |  |  | 110 |  |  |  |  |
| TTG | TTT | TAC | ATC | AAC | CTT | TAC | CCA | GAT | TAT | GCA | GCT | ATC | AGC | AGG | GCG |
| Leu | Phe | Tyr | Ile | Asn | Leu | Tyr | Pro | Asp | Tyr | Ala | Ala | Ile | Ser | Arg | Ala |
| 115 |  |  |  |  | 120 |  |  |  |  | 125 |  |  |  |  | 130 |

897

| ATC | CTG | GAT | CTG | GTC | CTC | TAT | TAC | AAC | TGG | AAA | ACA | GTG | ACA | GTG | GTG |
|---|---|---|---|---|---|---|---|---|---|---|---|---|---|---|---|
| Ile | Leu | Asp | Leu | Val | Leu | Tyr | Tyr | Asn | Trp | Lys | Thr | Val | Thr | Val | Val |
|  |  |  |  | 135 |  |  |  |  | 140 |  |  |  |  | 145 |  |

945

| TAT | GAA | GAC | AGC | ACA | GGT | CTA | ATT | CGT | CTA | CAA | GAG | CTC | ATC | AAA | GCT |
|---|---|---|---|---|---|---|---|---|---|---|---|---|---|---|---|
| Tyr | Glu | Asp | Ser | Thr | Gly | Leu | Ile | Arg | Leu | Gln | Glu | Leu | Ile | Lys | Ala |
|  |  |  | 150 |  |  |  |  | 155 |  |  |  |  | 160 |  |  |

993

| CCC | TCC | AGA | TAT | AAT | ATT | AAA | ATC | AAA | ATC | CGC | CAG | CTG | CCC | TCT | GGG |
|---|---|---|---|---|---|---|---|---|---|---|---|---|---|---|---|
| Pro | Ser | Arg | Tyr | Asn | Ile | Lys | Ile | Lys | Ile | Arg | Gln | Leu | Pro | Ser | Gly |
|  |  | 165 |  |  |  |  | 170 |  |  |  |  | 175 |  |  |  |

1041

| AAT | AAA | GAT | GCC | AAG | CCT | TTA | CTC | AAG | GAG | ATG | AAG | AAA | GGC | AAG | GAG |
|---|---|---|---|---|---|---|---|---|---|---|---|---|---|---|---|
| Asn | Lys | Asp | Ala | Lys | Pro | Leu | Leu | Lys | Glu | Met | Lys | Lys | Gly | Lys | Glu |
|  | 180 |  |  |  |  | 185 |  |  |  |  | 190 |  |  |  |  |

1089

| TTC | TAT | GTG | ATA | TTT | GAT | TGT | TCA | CAT | GAA | ACA | GCC | GCT | GAA | ATC | CTT |
|---|---|---|---|---|---|---|---|---|---|---|---|---|---|---|---|
| Phe | Tyr | Val | Ile | Phe | Asp | Cys | Ser | His | Glu | Thr | Ala | Ala | Glu | Ile | Leu |
| 195 |  |  |  |  | 200 |  |  |  |  | 205 |  |  |  |  | 210 |

1137

| AAG | CAG | ATT | CTG | TTC | ATG | GGC | ATG | ATG | ACC | GAA | TAC | TAT | CAC | TAC | TTT |
|---|---|---|---|---|---|---|---|---|---|---|---|---|---|---|---|
| Lys | Gln | Ile | Leu | Phe | Met | Gly | Met | Met | Thr | Glu | Tyr | Tyr | His | Tyr | Phe |
|  |  |  |  | 215 |  |  |  |  | 220 |  |  |  |  | 225 |  |

1185

| TTC | ACA | ACC | CTG | GAC | TTA | TTT | GCT | TTG | GAT | CTG | GAA | CTC | TAT | AGG | TAC |
|---|---|---|---|---|---|---|---|---|---|---|---|---|---|---|---|
| Phe | Thr | Thr | Leu | Asp | Leu | Phe | Ala | Leu | Asp | Leu | Glu | Leu | Tyr | Arg | Tyr |
|  |  |  | 230 |  |  |  |  | 235 |  |  |  |  | 240 |  |  |

1233

| AGT | GGC | GTA | AAC | ATG | ACC | GGG | TTT | GGG | CTG | CTT | AAC | ATT | GAC | AAC | CCT |
|---|---|---|---|---|---|---|---|---|---|---|---|---|---|---|---|
| Ser | Gly | Val | Asn | Met | Thr | Gly | Phe | Gly | Leu | Leu | Asn | Ile | Asp | Asn | Pro |
|  |  | 245 |  |  |  |  | 250 |  |  |  |  | 255 |  |  |  |

1281

| CAC | GTG | TCA | TCC | ATC | ATT | GAG | AAG | TGG | TCC | ATG | GAG | AGA | CTG | CAG | GCC |
|---|---|---|---|---|---|---|---|---|---|---|---|---|---|---|---|
| His | Val | Ser | Ser | Ile | Ile | Glu | Lys | Trp | Ser | Met | Glu | Arg | Leu | Gln | Ala |
|  | 260 |  |  |  |  | 265 |  |  |  |  | 270 |  |  |  |  |

1329

| CCA | CCC | AGG | CCC | GAG | ACT | GGC | CTT | TTG | GAT | GGC | ATG | ATG | ACA | ACT | GAA |
|---|---|---|---|---|---|---|---|---|---|---|---|---|---|---|---|
| Pro | Pro | Arg | Pro | Glu | Thr | Gly | Leu | Leu | Asp | Gly | Met | Met | Thr | Thr | Glu |
| 275 |  |  |  |  | 280 |  |  |  |  | 285 |  |  |  |  | 290 |

1377

| GCG | GCT | CTG | ATG | TAC | GAT | GCT | GTG | TAC | ATG | GTG | GCC | ATT | GCC | TCG | CAC |
|---|---|---|---|---|---|---|---|---|---|---|---|---|---|---|---|
| Ala | Ala | Leu | Met | Tyr | Asp | Ala | Val | Tyr | Met | Val | Ala | Ile | Ala | Ser | His |
|  |  |  |  | 295 |  |  |  |  | 300 |  |  |  |  | 305 |  |

1425

| CGG | GCA | TCC | CAG | CTG | ACC | GTC | AGC | TCC | CTG | CAG | TGC | CAT | AGA | CAT | AAG |
|---|---|---|---|---|---|---|---|---|---|---|---|---|---|---|---|
| Arg | Ala | Ser | Gln | Leu | Thr | Val | Ser | Ser | Leu | Gln | Cys | His | Arg | His | Lys |
|  |  |  | 310 |  |  |  |  | 315 |  |  |  |  | 320 |  |  |

1473

| CCA | TGG | CGC | CTC | GGA | CCC | AGA | TTT | ATG | AAC | CTG | ATC | AAA | GAG | GCC | CGG |
|---|---|---|---|---|---|---|---|---|---|---|---|---|---|---|---|
| Pro | Trp | Arg | Leu | Gly | Pro | Arg | Phe | Met | Asn | Leu | Ile | Lys | Glu | Ala | Arg |
|  |  | 325 |  |  |  |  | 330 |  |  |  |  | 335 |  |  |  |

1521

| TGG | GAT | GGC | TTG | ACT | GGG | CAT | ATC | ACC | TTT | AAT | AAA | ACC | AAT | GGC | TTG |
|---|---|---|---|---|---|---|---|---|---|---|---|---|---|---|---|
| Trp | Asp | Gly | Leu | Thr | Gly | His | Ile | Thr | Phe | Asn | Lys | Thr | Asn | Gly | Leu |
|  | 340 |  |  |  |  | 345 |  |  |  |  | 350 |  |  |  |  |

1569

| AGG | AAG | GAT | TTT | GAT | CTG | GAC | ATT | ATT | AGT | CTC | AAA | GAG | GAA | GGA | ACT |
|---|---|---|---|---|---|---|---|---|---|---|---|---|---|---|---|
| Arg | Lys | Asp | Phe | Asp | Leu | Asp | Ile | Ile | Ser | Leu | Lys | Glu | Glu | Gly | Thr |
| 355 |  |  |  |  | 360 |  |  |  |  | 365 |  |  |  |  | 370 |

1617

| GAA | AAG | ATT | GGG | ATT | TGG | AAT | TCC | AAC | AGT | GGG | CTT | AAC | ATG | ACG | GAC |
|---|---|---|---|---|---|---|---|---|---|---|---|---|---|---|---|
| Glu | Lys | Ile | Gly | Ile | Trp | Asn | Ser | Asn | Ser | Gly | Leu | Asn | Met | Thr | Asp |
|  |  |  |  | 375 |  |  |  |  | 380 |  |  |  |  | 385 |  |

1665

| AGC | AAC | AAA | GAC | AAG | TCC | AGC | AAT | ATC | ACT | GAT | TCA | TTG | GCC | AAC | AGA |
|---|---|---|---|---|---|---|---|---|---|---|---|---|---|---|---|
| Ser | Asn | Lys | Asp | Lys | Ser | Ser | Asn | Ile | Thr | Asp | Ser | Leu | Ala | Asn | Arg |
|  |  |  | 390 |  |  |  |  | 395 |  |  |  |  | 400 |  |  |

1713

| ACA | CTC | ATT | GTC | ACC | ACC | ATT | CTG | GAA | GAA | CCC | TAT | GTT | ATG | TAC | AGG |
|---|---|---|---|---|---|---|---|---|---|---|---|---|---|---|---|
| Thr | Leu | Ile | Val | Thr | Thr | Ile | Leu | Glu | Glu | Pro | Tyr | Val | Met | Tyr | Arg |
|  |  | 405 |  |  |  |  | 410 |  |  |  |  | 415 |  |  |  |

1761

| AAA | TCT | GAT | AAG | CCT | CTA | TAT | GGA | AAT | GAC | AGA | TTT | GAA | GGA | TAT | TGC |
|---|---|---|---|---|---|---|---|---|---|---|---|---|---|---|---|
| Lys | Ser | Asp | Lys | Pro | Leu | Tyr | Gly | Asn | Asp | Arg | Phe | Glu | Gly | Tyr | Cys |

1809

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| CTA | GAC | CTG | TTG | AAA | GAA | TTG | TCA | AAC | ATC | CTG | GGT | TTC | ATT | TAT | GAT | 1857 |
| Leu | Asp | Leu | Leu | Lys | Glu | Leu | Ser | Asn | Ile | Leu | Gly | Phe | Ile | Tyr | Asp |      |
| 435 |     |     |     |     | 440 |     |     |     |     | 445 |     |     |     |     | 450 |      |
| GTT | AAA | CTA | GTT | CCC | GAT | GGC | AAA | TAT | GGG | GCC | CAG | AAT | GAC | AAA | GGG | 1905 |
| Val | Lys | Leu | Val | Pro | Asp | Gly | Lys | Tyr | Gly | Ala | Gln | Asn | Asp | Lys | Gly |      |
|     |     |     |     | 455 |     |     |     |     | 460 |     |     |     |     | 465 |     |      |
| GAG | TGG | AAC | GGG | ATG | GTT | AAA | GAA | CTC | ATA | GAT | CAC | AGG | GCT | GAC | CTG | 1953 |
| Glu | Trp | Asn | Gly | Met | Val | Lys | Glu | Leu | Ile | Asp | His | Arg | Ala | Asp | Leu |      |
|     |     |     | 470 |     |     |     |     | 475 |     |     |     |     | 480 |     |     |      |
| GCA | GTG | GCT | CCT | CTT | ACC | ATC | ACC | TAC | GTG | CGG | GAG | AAA | GTC | ATT | GAC | 2001 |
| Ala | Val | Ala | Pro | Leu | Thr | Ile | Thr | Tyr | Val | Arg | Glu | Lys | Val | Ile | Asp |      |
|     |     | 485 |     |     |     |     | 490 |     |     |     |     | 495 |     |     |     |      |
| TTC | TCC | AAA | CCC | TTC | ATG | ACC | CTA | GGC | ATC | AGC | ATT | CTC | TAC | CGG | AAG | 2049 |
| Phe | Ser | Lys | Pro | Phe | Met | Thr | Leu | Gly | Ile | Ser | Ile | Leu | Tyr | Arg | Lys |      |
|     |     | 500 |     |     |     | 505 |     |     |     |     | 510 |     |     |     |     |      |
| CCC | AAT | GGT | ACC | AAT | CCA | GGC | GTT | TTC | TCC | TTC | CTC | AAC | CCC | CTG | TCT | 2097 |
| Pro | Asn | Gly | Thr | Asn | Pro | Gly | Val | Phe | Ser | Phe | Leu | Asn | Pro | Leu | Ser |      |
| 515 |     |     |     |     | 520 |     |     |     |     | 525 |     |     |     |     | 530 |      |
| CCA | GAT | ATT | TGG | ATG | TAT | GTG | CTC | TTA | GCC | TGC | TTG | GGA | GTC | AGC | TGT | 2145 |
| Pro | Asp | Ile | Trp | Met | Tyr | Val | Leu | Leu | Ala | Cys | Leu | Gly | Val | Ser | Cys |      |
|     |     |     |     | 535 |     |     |     |     | 540 |     |     |     |     | 545 |     |      |
| GTA | CTC | TTT | GTG | ATT | GCA | AGG | TTT | ACA | CCC | TAC | GAG | TGG | TAT | AAC | CCC | 2193 |
| Val | Leu | Phe | Val | Ile | Ala | Arg | Phe | Thr | Pro | Tyr | Glu | Trp | Tyr | Asn | Pro |      |
|     |     |     | 550 |     |     |     |     | 555 |     |     |     |     | 560 |     |     |      |
| CAC | CCA | TGC | AAC | CCT | GAC | TCA | GAC | GTG | GTG | GAA | AAC | AAT | TTT | ACT | TTA | 2241 |
| His | Pro | Cys | Asn | Pro | Asp | Ser | Asp | Val | Val | Glu | Asn | Asn | Phe | Thr | Leu |      |
|     |     | 565 |     |     |     |     | 570 |     |     |     |     | 575 |     |     |     |      |
| CTA | AAT | AGT | TTC | TGG | TTT | GGA | GTT | GGA | GCT | CTC | ATG | CAG | CAA | GGA | TCA | 2289 |
| Leu | Asn | Ser | Phe | Trp | Phe | Gly | Val | Gly | Ala | Leu | Met | Gln | Gln | Gly | Ser |      |
| 580 |     |     |     |     | 585 |     |     |     |     |     | 590 |     |     |     |     |      |
| GAG | CTG | ATG | CCC | AAA | GCT | CTA | TCG | ACC | AGA | ATA | GTT | GGA | GGG | ATA | TGG | 2337 |
| Glu | Leu | Met | Pro | Lys | Ala | Leu | Ser | Thr | Arg | Ile | Val | Gly | Gly | Ile | Trp |      |
| 595 |     |     |     |     | 600 |     |     |     |     | 605 |     |     |     |     | 610 |      |
| TGG | TTT | TTC | ACC | CTA | ATC | ATC | ATT | TCA | TCC | TAC | ACG | GCC | AAT | CTG | GCT | 2385 |
| Trp | Phe | Phe | Thr | Leu | Ile | Ile | Ile | Ser | Ser | Tyr | Thr | Ala | Asn | Leu | Ala |      |
|     |     |     |     | 615 |     |     |     |     | 620 |     |     |     |     | 625 |     |      |
| GCC | TTC | TTG | ACA | GTA | GAG | AGA | ATG | GAA | TCC | CCC | ATA | GAT | TCG | GCA | GAT | 2433 |
| Ala | Phe | Leu | Thr | Val | Glu | Arg | Met | Glu | Ser | Pro | Ile | Asp | Ser | Ala | Asp |      |
|     |     |     | 630 |     |     |     |     | 635 |     |     |     |     | 640 |     |     |      |
| GAT | CTG | GCA | AAG | CAA | ACC | AAG | ATA | GAA | TAT | GGG | GCG | GTT | AGA | GAT | GGA | 2481 |
| Asp | Leu | Ala | Lys | Gln | Thr | Lys | Ile | Glu | Tyr | Gly | Ala | Val | Arg | Asp | Gly |      |
|     |     | 645 |     |     |     |     | 650 |     |     |     |     | 655 |     |     |     |      |
| TCA | ACA | ATG | ACC | TTC | TTC | AAG | AAA | TCA | AAA | ATC | TCC | ACC | TAT | GAG | AAG | 2529 |
| Ser | Thr | Met | Thr | Phe | Phe | Lys | Lys | Ser | Lys | Ile | Ser | Thr | Tyr | Glu | Lys |      |
| 660 |     |     |     |     | 665 |     |     |     |     | 670 |     |     |     |     |     |      |
| ATG | TGG | GCT | TTC | ATG | AGC | AGC | AGG | CAG | CAG | ACC | GCC | CTG | GTA | AGA | AAC | 2577 |
| Met | Trp | Ala | Phe | Met | Ser | Ser | Arg | Gln | Gln | Thr | Ala | Leu | Val | Arg | Asn |      |
| 675 |     |     |     |     | 680 |     |     |     |     | 685 |     |     |     |     | 690 |      |
| AGT | GAT | GAG | GGG | ATC | CAG | AGA | GTG | CTC | ACC | ACA | GAC | TAC | GCG | CTG | CTG | 2625 |
| Ser | Asp | Glu | Gly | Ile | Gln | Arg | Val | Leu | Thr | Thr | Asp | Tyr | Ala | Leu | Leu |      |
|     |     |     |     | 695 |     |     |     |     | 700 |     |     |     |     | 705 |     |      |
| ATG | GAG | TCC | ACC | AGC | ATT | GAG | TAT | GTG | ACG | CAG | AGA | AAC | TGC | AAC | CTC | 2673 |
| Met | Glu | Ser | Thr | Ser | Ile | Glu | Tyr | Val | Thr | Gln | Arg | Asn | Cys | Asn | Leu |      |
|     |     |     | 710 |     |     |     |     | 715 |     |     |     |     | 720 |     |     |      |
| ACT | CAG | ATC | GGG | GGC | CTC | ATT | GAC | TCC | AAA | GGT | TAC | GGA | GTG | GGA | ACA | 2721 |
| Thr | Gln | Ile | Gly | Gly | Leu | Ile | Asp | Ser | Lys | Gly | Tyr | Gly | Val | Gly | Thr |      |
|     |     | 725 |     |     |     |     | 730 |     |     |     |     | 735 |     |     |     |      |
| CCT | ATT | GGT | TCT | CCT | TAC | CGG | GAT | AAA | ATT | ACT | ATT | GCT | ATT | CTT | CAA | 2769 |
| Pro | Ile | Gly | Ser | Pro | Tyr | Arg | Asp | Lys | Ile | Thr | Ile | Ala | Ile | Leu | Gln |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 740 |     |     |     |     | 745 |     |     |     |     | 750 |     |     |      |
| CTC | CAA | GAA | GAA | GGG | AAG | CTG | CAT | ATG | ATG | AAA | GAG | AAG | TGG | TGG | CGT | 2817 |
| Leu | Gln | Glu | Glu | Gly | Lys | Leu | His | Met | Met | Lys | Glu | Lys | Trp | Trp | Arg |      |
| 755 |     |     |     |     | 760 |     |     |     |     | 765 |     |     |     |     | 770 |      |
| GGG | AAT | GGC | TGC | CCC | GAG | GAA | GAC | AAC | AAA | GAA | GCC | AGT | GCC | CTG | GGA | 2865 |
| Gly | Asn | Gly | Cys | Pro | Glu | Glu | Asp | Asn | Lys | Glu | Ala | Ser | Ala | Leu | Gly |      |
|     |     |     |     | 775 |     |     |     |     | 780 |     |     |     |     | 785 |     |      |
| GTG | GAA | AAT | ATT | GGA | GGC | ATC | TTC | ATT | GTT | CTG | GCT | GCC | GGA | CTG | GTC | 2913 |
| Val | Glu | Asn | Ile | Gly | Gly | Ile | Phe | Ile | Val | Leu | Ala | Ala | Gly | Leu | Val |      |
|     |     |     | 790 |     |     |     |     | 795 |     |     |     |     | 800 |     |     |      |
| CTT | TCT | GTA | TTT | GTA | GCT | ATT | GGA | GAA | TTC | ATA | TAC | AAA | TCA | CGG | AAG | 2961 |
| Leu | Ser | Val | Phe | Val | Ala | Ile | Gly | Glu | Phe | Ile | Tyr | Lys | Ser | Arg | Lys |      |
|     |     | 805 |     |     |     |     | 810 |     |     |     |     | 815 |     |     |     |      |
| AAT | AAT | GAT | ATT | GAA | CAG | TGT | CTC | TCT | TTC | AAC | GCT | ATC | ATG | GAA | GAA | 3009 |
| Asn | Asn | Asp | Ile | Glu | Gln | Cys | Leu | Ser | Phe | Asn | Ala | Ile | Met | Glu | Glu |      |
|     | 820 |     |     |     |     | 825 |     |     |     |     | 830 |     |     |     |     |      |
| CTG | GGA | ATC | TCA | CTG | AAG | AAT | CAG | AAA | AAA | ATA | AAG | AAA | AAG | TCA | AGA | 3057 |
| Leu | Gly | Ile | Ser | Leu | Lys | Asn | Gln | Lys | Lys | Ile | Lys | Lys | Lys | Ser | Arg |      |
| 835 |     |     |     |     | 840 |     |     |     |     | 845 |     |     |     |     | 850 |      |
| ACT | AAG | GGG | AAA | TCT | TCC | TTC | ACA | AGT | ATC | CTT | ACT | TGT | CAT | CAG | AGA | 3105 |
| Thr | Lys | Gly | Lys | Ser | Ser | Phe | Thr | Ser | Ile | Leu | Thr | Cys | His | Gln | Arg |      |
|     |     |     |     | 855 |     |     |     |     | 860 |     |     |     |     | 865 |     |      |
| CGA | ACT | CAG | AGA | AAA | GAG | ACT | GTG | GCG | TGATCCAAGG | AAACGCCTGT | | | | | | 3152 |
| Arg | Thr | Gln | Arg | Lys | Glu | Thr | Val | Ala |     |     |     |     |     |     |     |      |
|     |     | 870 |     |     |     |     | 875 |     |     |     |     |     |     |     |     |      |

| AGGAAGAAAA | AGGATGCATT | CCCTACAGAT | TTTTGGAGAA | AGGATTTCTG | AGGAGTTGTG | 3212 |
| TGATGTGTTT | CCATATATCT | ATATCCATAA | CTCTGATTAT | GAATACAGAT | ATAAGAAATA | 3272 |
| CAAAAGTTTA | AAAAGCTCAC | ATAGATATGA | CTTGGGAAGT | GACACCAGTT | CTTTTAAAAT | 3332 |
| AAATTTGTAT | GCACAAAAAA | AAAAAAAAAA | AAAAAAAAAA | AAAAAAGGAA | TTC .      | 3385 |

( 2 ) INFORMATION FOR SEQ ID NO:2:

( i ) SEQUENCE CHARACTERISTICS:
        ( A ) LENGTH: 905 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Glu | His | Gly | Thr | Leu | Leu | Ala | Gln | Pro | Gly | Leu | Trp | Thr | Arg | Asp |
|-----|-----|-----|-----|-----|-----|-----|-----|-----|-----|-----|-----|-----|-----|-----|-----|
| -30 |     |     |     |     | -25 |     |     |     |     | -20 |     |     |     |     | -15 |
| Thr | Ser | Trp | Ala | Leu | Leu | Tyr | Phe | Leu | Cys | Tyr | Ile | Leu | Pro | Gln | Thr |
|     |     |     |     | -10 |     |     |     |     | -5  |     |     |     |     |     | 1   |
| Ala | Pro | Gln | Val | Leu | Arg | Ile | Gly | Gly | Ile | Phe | Glu | Thr | Val | Glu | Asn |
|     |     | 5   |     |     |     |     | 10  |     |     |     |     | 15  |     |     |     |
| Glu | Pro | Val | Asn | Val | Glu | Glu | Leu | Ala | Phe | Lys | Phe | Ala | Val | Thr | Ser |
|     | 20  |     |     |     |     | 25  |     |     |     |     | 30  |     |     |     |     |
| Ile | Asn | Arg | Asn | Arg | Thr | Leu | Met | Pro | Asn | Thr | Thr | Leu | Thr | Tyr | Asp |
| 35  |     |     |     |     | 40  |     |     |     |     | 45  |     |     |     |     | 50  |
| Ile | Gln | Arg | Ile | Asn | Leu | Phe | Asp | Ser | Phe | Glu | Ala | Ser | Arg | Arg | Ala |
|     |     |     |     | 55  |     |     |     |     | 60  |     |     |     |     | 65  |     |
| Cys | Asp | Gln | Leu | Ala | Leu | Gly | Val | Ala | Ala | Leu | Phe | Gly | Pro | Ser | His |
|     |     |     | 70  |     |     |     |     | 75  |     |     |     |     | 80  |     |     |
| Ser | Ser | Ser | Val | Ser | Ala | Val | Gln | Ser | Ile | Cys | Asn | Ala | Leu | Glu | Val |
|     |     | 85  |     |     |     |     | 90  |     |     |     |     | 95  |     |     |     |
| Pro | His | Ile | Gln | Thr | Arg | Trp | Lys | His | Pro | Ser | Val | Asp | Asn | Lys | Asp |
|     | 100 |     |     |     |     | 105 |     |     |     |     | 110 |     |     |     |     |

-continued

| | | | | | | | | | | | | | | | |
|---|---|---|---|---|---|---|---|---|---|---|---|---|---|---|---|
| Leu | Phe | Tyr | Ile | Asn | Leu | Tyr | Pro | Asp | Tyr | Ala | Ala | Ile | Ser | Arg | Ala |
| 115 | | | | 120 | | | | 125 | | | | | | | 130 |
| Ile | Leu | Asp | Leu | Val | Leu | Tyr | Tyr | Asn | Trp | Lys | Thr | Val | Thr | Val | Val |
| | | | | 135 | | | | 140 | | | | | 145 | | |
| Tyr | Glu | Asp | Ser | Thr | Gly | Leu | Ile | Arg | Leu | Gln | Glu | Leu | Ile | Lys | Ala |
| | | | 150 | | | | 155 | | | | | 160 | | | |
| Pro | Ser | Arg | Tyr | Asn | Ile | Lys | Ile | Lys | Ile | Arg | Gln | Leu | Pro | Ser | Gly |
| | | 165 | | | | 170 | | | | | 175 | | | | |
| Asn | Lys | Asp | Ala | Lys | Pro | Leu | Leu | Lys | Glu | Met | Lys | Lys | Gly | Lys | Glu |
| | 180 | | | | 185 | | | | | 190 | | | | | |
| Phe | Tyr | Val | Ile | Phe | Asp | Cys | Ser | His | Glu | Thr | Ala | Ala | Glu | Ile | Leu |
| 195 | | | | 200 | | | | 205 | | | | | | | 210 |
| Lys | Gln | Ile | Leu | Phe | Met | Gly | Met | Met | Thr | Glu | Tyr | Tyr | His | Tyr | Phe |
| | | | | 215 | | | | 220 | | | | | 225 | | |
| Phe | Thr | Thr | Leu | Asp | Leu | Phe | Ala | Leu | Asp | Leu | Glu | Leu | Tyr | Arg | Tyr |
| | | | 230 | | | | 235 | | | | | 240 | | | |
| Ser | Gly | Val | Asn | Met | Thr | Gly | Phe | Gly | Leu | Leu | Asn | Ile | Asp | Asn | Pro |
| | | 245 | | | | 250 | | | | | 255 | | | | |
| His | Val | Ser | Ser | Ile | Ile | Glu | Lys | Trp | Ser | Met | Glu | Arg | Leu | Gln | Ala |
| | 260 | | | | 265 | | | | | 270 | | | | | |
| Pro | Pro | Arg | Pro | Glu | Thr | Gly | Leu | Leu | Asp | Gly | Met | Met | Thr | Thr | Glu |
| 275 | | | | 280 | | | | 285 | | | | | | | 290 |
| Ala | Ala | Leu | Met | Tyr | Asp | Ala | Val | Tyr | Met | Val | Ala | Ile | Ala | Ser | His |
| | | | | 295 | | | | 300 | | | | | 305 | | |
| Arg | Ala | Ser | Gln | Leu | Thr | Val | Ser | Ser | Leu | Gln | Cys | His | Arg | His | Lys |
| | | | 310 | | | | 315 | | | | | 320 | | | |
| Pro | Trp | Arg | Leu | Gly | Pro | Arg | Phe | Met | Asn | Leu | Ile | Lys | Glu | Ala | Arg |
| | | 325 | | | | 330 | | | | | 335 | | | | |
| Trp | Asp | Gly | Leu | Thr | Gly | His | Ile | Thr | Phe | Asn | Lys | Thr | Asn | Gly | Leu |
| | 340 | | | | 345 | | | | | 350 | | | | | |
| Arg | Lys | Asp | Phe | Asp | Leu | Asp | Ile | Ile | Ser | Leu | Lys | Glu | Glu | Gly | Thr |
| 355 | | | | 360 | | | | 365 | | | | | | | 370 |
| Glu | Lys | Ile | Gly | Ile | Trp | Asn | Ser | Asn | Ser | Gly | Leu | Asn | Met | Thr | Asp |
| | | | | 375 | | | | 380 | | | | | 385 | | |
| Ser | Asn | Lys | Asp | Lys | Ser | Ser | Asn | Ile | Thr | Asp | Ser | Leu | Ala | Asn | Arg |
| | | | 390 | | | | 395 | | | | | 400 | | | |
| Thr | Leu | Ile | Val | Thr | Thr | Ile | Leu | Glu | Glu | Pro | Tyr | Val | Met | Tyr | Arg |
| | | 405 | | | | 410 | | | | | 415 | | | | |
| Lys | Ser | Asp | Lys | Pro | Leu | Tyr | Gly | Asn | Asp | Arg | Phe | Glu | Gly | Tyr | Cys |
| | 420 | | | | 425 | | | | | 430 | | | | | |
| Leu | Asp | Leu | Leu | Lys | Glu | Leu | Ser | Asn | Ile | Leu | Gly | Phe | Ile | Tyr | Asp |
| 435 | | | | 440 | | | | 445 | | | | | | | 450 |
| Val | Lys | Leu | Val | Pro | Asp | Gly | Lys | Tyr | Gly | Ala | Gln | Asn | Asp | Lys | Gly |
| | | | | 455 | | | | 460 | | | | | 465 | | |
| Glu | Trp | Asn | Gly | Met | Val | Lys | Glu | Leu | Ile | Asp | His | Arg | Ala | Asp | Leu |
| | | | 470 | | | | 475 | | | | | 480 | | | |
| Ala | Val | Ala | Pro | Leu | Thr | Ile | Thr | Tyr | Val | Arg | Glu | Lys | Val | Ile | Asp |
| | | 485 | | | | 490 | | | | | 495 | | | | |
| Phe | Ser | Lys | Pro | Phe | Met | Thr | Leu | Gly | Ile | Ser | Ile | Leu | Tyr | Arg | Lys |
| | 500 | | | | 505 | | | | | 510 | | | | | |
| Pro | Asn | Gly | Thr | Asn | Pro | Gly | Val | Phe | Ser | Phe | Leu | Asn | Pro | Leu | Ser |
| 515 | | | | 520 | | | | 525 | | | | | | | 530 |
| Pro | Asp | Ile | Trp | Met | Tyr | Val | Leu | Leu | Ala | Cys | Leu | Gly | Val | Ser | Cys |

|     |     |     | 535 |     |     |     |     | 540 |     |     |     |     | 545 |     |     |
| --- | --- | --- | --- | --- | --- | --- | --- | --- | --- | --- | --- | --- | --- | --- | --- |
| Val | Leu | Phe | Val<br>550 | Ile | Ala | Arg | Phe | Thr<br>555 | Pro | Tyr | Glu | Trp | Tyr<br>560 | Asn | Pro |
| His | Pro | Cys<br>565 | Asn | Pro | Asp | Ser | Asp<br>570 | Val | Val | Glu | Asn | Asn<br>575 | Phe | Thr | Leu |
| Leu | Asn<br>580 | Ser | Phe | Trp | Phe | Gly<br>585 | Val | Gly | Ala | Leu | Met<br>590 | Gln | Gln | Gly | Ser |
| Glu<br>595 | Leu | Met | Pro | Lys | Ala<br>600 | Leu | Ser | Thr | Arg | Ile<br>605 | Val | Gly | Gly | Ile | Trp<br>610 |
| Trp | Phe | Phe | Thr | Leu<br>615 | Ile | Ile | Ile | Ser | Ser<br>620 | Tyr | Thr | Ala | Asn | Leu<br>625 | Ala |
| Ala | Phe | Leu | Thr<br>630 | Val | Glu | Arg | Met | Glu<br>635 | Ser | Pro | Ile | Asp | Ser<br>640 | Ala | Asp |
| Asp | Leu | Ala<br>645 | Lys | Gln | Thr | Lys | Ile<br>650 | Glu | Tyr | Gly | Ala | Val<br>655 | Arg | Asp | Gly |
| Ser | Thr<br>660 | Met | Thr | Phe | Phe | Lys<br>665 | Lys | Ser | Lys | Ile | Ser<br>670 | Thr | Tyr | Glu | Lys |
| Met<br>675 | Trp | Ala | Phe | Met | Ser<br>680 | Ser | Arg | Gln | Gln | Thr<br>685 | Ala | Leu | Val | Arg | Asn<br>690 |
| Ser | Asp | Glu | Gly | Ile<br>695 | Gln | Arg | Val | Leu | Thr<br>700 | Thr | Asp | Tyr | Ala | Leu<br>705 | Leu |
| Met | Glu | Ser | Thr<br>710 | Ser | Ile | Glu | Tyr | Val<br>715 | Thr | Gln | Arg | Asn | Cys<br>720 | Asn | Leu |
| Thr | Gln | Ile<br>725 | Gly | Gly | Leu | Ile | Asp<br>730 | Ser | Lys | Gly | Tyr | Gly<br>735 | Val | Gly | Thr |
| Pro | Ile<br>740 | Gly | Ser | Pro | Tyr | Arg<br>745 | Asp | Lys | Ile | Thr | Ile<br>750 | Ala | Ile | Leu | Gln |
| Leu<br>755 | Gln | Glu | Glu | Gly | Lys<br>760 | Leu | His | Met | Met | Lys<br>765 | Glu | Lys | Trp | Trp | Arg<br>770 |
| Gly | Asn | Gly | Cys | Pro<br>775 | Glu | Glu | Asp | Asn | Lys<br>780 | Glu | Ala | Ser | Ala | Leu<br>785 | Gly |
| Val | Glu | Asn | Ile<br>790 | Gly | Gly | Ile | Phe | Ile<br>795 | Val | Leu | Ala | Ala | Gly<br>800 | Leu | Val |
| Leu | Ser | Val<br>805 | Phe | Val | Ala | Ile | Gly<br>810 | Glu | Phe | Ile | Tyr | Lys<br>815 | Ser | Arg | Lys |
| Asn | Asn<br>820 | Asp | Ile | Glu | Gln | Cys<br>825 | Leu | Ser | Phe | Asn | Ala<br>830 | Ile | Met | Glu | Glu |
| Leu<br>835 | Gly | Ile | Ser | Leu | Lys<br>840 | Asn | Gln | Lys | Lys | Ile<br>845 | Lys | Lys | Lys | Ser | Arg<br>850 |
| Thr | Lys | Gly | Lys | Ser<br>855 | Ser | Phe | Thr | Ser | Ile<br>860 | Leu | Thr | Cys | His | Gln<br>865 | Arg |
| Arg | Thr | Gln | Arg<br>870 | Lys | Glu | Thr | Val | Ala<br>875 |     |     |     |     |     |     |     |

(2) INFORMATION FOR SEQ ID NO:3:

(i) SEQUENCE CHARACTERISTICS:
(A) LENGTH: 50 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:3:

Ala Ala Phe Leu Thr Val Glu Arg Met Glu Ser Pro Ile Asn Ser Ala

```
            1                    5                      10                       15
```

Asp Asp Leu Ala Lys Gln Thr Lys Ile Glu Tyr Gly Ala Val Arg Asp
            20                          25                       30

Gly Ser Thr Met Thr Phe Phe Lys Lys Ser Lys Ile Ser Thr Tyr Glu
            35                          40                       45

Lys Met
    50

( 2 ) INFORMATION FOR SEQ ID NO:4:

( i ) SEQUENCE CHARACTERISTICS:
        ( A ) LENGTH: 50 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:4:

Ala Ala Phe Leu Thr Val Glu Arg Met Glu Ser Pro Ile Asp Ser Ala
 1               5                      10                      15

Asp Asp Leu Ala Lys Gln Thr Lys Ile Glu Tyr Gly Ala Val Arg Asp
            20                          25                       30

Gly Ser Thr Met Thr Phe Phe Lys Lys Ser Lys Ile Ser Thr Tyr Glu
            35                          40                       45

Lys Met
    50

( 2 ) INFORMATION FOR SEQ ID NO:5:

( i ) SEQUENCE CHARACTERISTICS:
        ( A ) LENGTH: 50 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

GAGAGAATGG AATCCCCCAT AAATTCGGCA GATGATCTGG CAAAGCAAAC    50

( 2 ) INFORMATION FOR SEQ ID NO:6:

( i ) SEQUENCE CHARACTERISTICS:
        ( A ) LENGTH: 50 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:6:

GAGAGAATGG AATCCCCCAT AGATTCGGCA GATGATCTGG CAAAGCAAAC    50

( 2 ) INFORMATION FOR SEQ ID NO:7:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( v ) FRAGMENT TYPE: C-terminal ( x i ) SEQUENCE DESCRIPTION: SEQ ID NO:7:

```
Ala  Ala  Gly  Leu  Val  Leu  Ser  Val  Phe  Val  Ala  Ile  Gly  Glu  Phe  Ile
 1              5                        10                       15

Tyr  Lys  Ser  Arg  Lys  Asn  Asn  Asp  Ile  Glu  Gln  Val  Ser  His  Leu  Phe
              20                       25                       30

Leu  Gly  Leu  Val  Ser  Leu
              35
```

(2) INFORMATION FOR SEQ ID NO:8:

(i) SEQUENCE CHARACTERISTICS:
        (A) LENGTH: 50 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:8:

```
Ala  Ala  Gly  Leu  Val  Leu  Ser  Val  Phe  Val  Ala  Ile  Gly  Glu  Phe  Ile
 1              5                        10                       15

Tyr  Lys  Ser  Arg  Lys  Asn  Asn  Asp  Ile  Glu  Gln  Cys  Leu  Ser  Phe  Asn
              20                       25                       30

Ala  Ile  Met  Glu  Glu  Leu  Gly  Ile  Ser  Leu  Lys  Asn  Gln  Lys  Lys  Ile
              35                       40                       45

Lys  Lys
     50
```

(2) INFORMATION FOR SEQ ID NO:9:

(i) SEQUENCE CHARACTERISTICS:
        (A) LENGTH: 119 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:9:

```
CAAATCACGG  AAGAATAATG  ATATTGAACA  GGTGAGTCAT  CTCTTTCTAG  GACTGGTTAG    60
TTTATAGTTT  GCATTATCTG  TCTTAAGTTT  GGGGGTTTTT  AAGGATGTTT  GCTCTTTTT    119
```

(2) INFORMATION FOR SEQ ID NO:10:

(i) SEQUENCE CHARACTERISTICS:
        (A) LENGTH: 124 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

```
CAAATCACGG  AAGAATAATG  ATATTGAACA  GTGTCTCTCT  TTCAACGCTA  TCATGGAAGA    60
ACTGGGAATC  TCACTGAAGA  ATCAGAAAAA  AATAAAGAAA  AAGTCAAGAA  CTAAGGGGAA   120
ATCT                                                                    124
```

(2) INFORMATION FOR SEQ ID NO:11:

(i) SEQUENCE CHARACTERISTICS:
        (A) LENGTH: 44 amino acids
        (B) TYPE: amino acid
        (D) TOPOLOGY: linear ( i i ) MOLECULE TYPE: peptide ( v ) FRAGMENT TYPE: N-terminal ( i x ) FEATURE:
  ( A ) NAME/KEY: Peptide
  ( B ) LOCATION: 1..29
  ( D ) OTHER INFORMATION: /note="Signal Peptide"

( x i ) SEQUENCE DESCRIPTION: SEQ ID NO:11:

| Met | Glu | His | Gly | Thr | Leu | Leu | Ala | Gln | Pro | Gly | Leu | Trp | Thr | Arg | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Ser | Trp | Gly | Leu | Leu | Tyr | Phe | Leu | Cys | Tyr | Ile | Leu | Pro | Gln | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ala | Pro | Gln | Val | Leu | Arg | Ile | Ala | Cys | Asp | Gln | Leu |
|-----|-----|-----|-----|-----|-----|-----|-----|-----|-----|-----|-----|
|     |     | 35  |     |     |     |     | 40  |     |     |     |     |

( 2 ) INFORMATION FOR SEQ ID NO:12:

( i ) SEQUENCE CHARACTERISTICS:
    ( A ) LENGTH: 100 amino acids
    ( B ) TYPE: amino acid
    ( D ) TOPOLOGY: linear ( i i ) MOLECULE TYPE: peptide ( v ) FRAGMENT TYPE: N-terminal ( i x ) FEATURE:
    ( A ) NAME/KEY: Peptide
    ( B ) LOCATION: 1..29
    ( D ) OTHER INFORMATION: /note="Signal Peptide"

( x i ) SEQUENCE DESCRIPTION: SEQ ID NO:12:

| Met | Glu | His | Gly | Thr | Leu | Leu | Ala | Gln | Pro | Gly | Leu | Trp | Thr | Arg | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Ser | Trp | Gly | Leu | Leu | Tyr | Phe | Leu | Cys | Tyr | Ile | Leu | Pro | Gln | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ala | Pro | Gln | Val | Leu | Arg | Ile | Gly | Gly | Ile | Phe | Glu | Thr | Val | Glu | Asn |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Glu | Pro | Val | Asn | Val | Glu | Glu | Leu | Ala | Phe | Lys | Phe | Ala | Val | Thr | Ser |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ile | Asn | Arg | Asn | Arg | Thr | Leu | Met | Pro | Asn | Thr | Thr | Leu | Thr | Tyr | Asp |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ile | Gln | Arg | Ile | Asn | Leu | Phe | Asp | Ser | Phe | Glu | Val | Leu | Arg | Ile | Ala |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Cys | Asp | Gln | Leu |
|-----|-----|-----|-----|
|     |     |     | 100 |

( 2 ) INFORMATION FOR SEQ ID NO:13:

( i ) SEQUENCE CHARACTERISTICS:
    ( A ) LENGTH: 82 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:13:

```
ATCCTCCCTC AGACCGCCCC GCAAGTACTC AGGATCGCAT GTGACCAGCT GGCTCTTGGT    60
GTGGCTGCTC TCTTTGGCCC TT                                             82
```

( 2 ) INFORMATION FOR SEQ ID NO:14:

(i) SEQUENCE CHARACTERISTICS:
    (A) LENGTH: 100 base pairs
    (B) TYPE: nucleic acid
    (C) STRANDEDNESS: double
    (D) TOPOLOGY: linear (ii) MOLECULE TYPE: cDNA (xi) SEQUENCE DESCRIPTION: SEQ ID NO:14:

ATCCTCCCTC AGACCGCCCC GCAAGTACTC AGGATCGGAG GGATTTTTGA GAGAGCATGT 60

GACCAGCTGG CTCTTGGTGT GGCTGCTCTC TTTGGCCCTT 100

(2) INFORMATION FOR SEQ ID NO:15:

(i) SEQUENCE CHARACTERISTICS:
    (A) LENGTH: 40 base pairs
    (B) TYPE: nucleic acid
    (C) STRANDEDNESS: single
    (D) TOPOLOGY: linear (xi) SEQUENCE DESCRIPTION: SEQ ID NO:15:

ATCGGCGGCA TCTTCATTGT TCTGGCTGCA GGACTCGTGC 40

(2) INFORMATION FOR SEQ ID NO:16:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (xi) SEQUENCE DESCRIPTION: SEQ ID NO:16:

CCATCATTGA GAAGTGGTCC 20

(2) INFORMATION FOR SEQ ID NO:17:

(i) SEQUENCE CHARACTERISTICS:
    (A) LENGTH: 866 amino acids
    (B) TYPE: amino acid
    (D) TOPOLOGY: linear (ii) MOLECULE TYPE: protein (xi) SEQUENCE DESCRIPTION: SEQ ID NO:17:

```
Met Glu His Gly Thr Leu Leu Ala Gln Pro Gly Leu Trp Thr Arg Asp
-30              -25             -20             -15

Thr Ser Trp Ala Leu Leu Tyr Phe Leu Cys Tyr Ile Leu Pro Gln Thr
             -10              -5                       1

Ala Pro Gln Val Leu Arg Ile Gly Gly Ile Phe Glu Thr Val Glu Asn
         5               10              15

Glu Pro Val Asn Val Glu Glu Leu Ala Phe Lys Phe Ala Val Thr Ser
     20              25              30

Ile Asn Arg Asn Arg Thr Leu Met Pro Asn Thr Thr Leu Thr Tyr Asp
35              40              45                       50

Ile Gln Arg Ile Asn Leu Phe Asp Ser Phe Glu Ala Ser Arg Arg Ala
             55              60                       65

Cys Asp Gln Leu Ala Leu Gly Val Ala Ala Leu Phe Gly Pro Ser His
         70              75              80

Ser Ser Ser Val Ser Ala Val Gln Ser Ile Cys Asn Ala Leu Glu Val
             85              90              95

Pro His Ile Gln Thr Arg Trp Lys His Pro Ser Val Asp Asn Lys Asp
    100             105             110

Leu Phe Tyr Ile Asn Leu Tyr Pro Asp Tyr Ala Ala Ile Ser Arg Ala
```

```
                    115                           120                           125                           130
         Ile  Leu  Asp  Leu  Val  Leu  Tyr  Tyr  Asn  Trp  Lys  Thr  Val  Thr  Val  Val
                             135                           140                           145

Tyr  Glu  Asp  Ser  Thr  Gly  Leu  Ile  Arg  Leu  Gln  Glu  Leu  Ile  Lys  Ala
                             150                           155                           160

Pro  Ser  Arg  Tyr  Asn  Ile  Lys  Ile  Lys  Ile  Arg  Gln  Leu  Pro  Ser  Gly
                        165                      170                           175

Asn  Lys  Asp  Ala  Lys  Pro  Leu  Lys  Glu  Met  Lys  Lys  Gly  Lys  Glu
              180                      185                           190

Phe  Tyr  Val  Ile  Phe  Asp  Cys  Ser  His  Glu  Thr  Ala  Ala  Glu  Ile  Leu
         195                           200                           205                           210

Lys  Gln  Ile  Leu  Phe  Met  Gly  Met  Met  Thr  Glu  Tyr  Tyr  His  Tyr  Phe
                             215                           220                           225

Phe  Thr  Thr  Leu  Asp  Leu  Phe  Ala  Leu  Asp  Leu  Glu  Leu  Tyr  Arg  Tyr
                             230                           235                                240

Ser  Gly  Val  Asn  Met  Thr  Gly  Phe  Gly  Leu  Leu  Asn  Ile  Asp  Asn  Pro
                        245                      250                           255

His  Val  Ser  Ser  Ile  Ile  Glu  Lys  Trp  Ser  Met  Glu  Arg  Leu  Gln  Ala
              260                      265                           270

Pro  Pro  Arg  Pro  Glu  Thr  Gly  Leu  Leu  Asp  Gly  Met  Met  Thr  Thr  Glu
         275                           280                           285                           290

Ala  Ala  Leu  Met  Tyr  Asp  Ala  Val  Tyr  Met  Val  Ala  Ile  Ala  Ser  His
                             295                           300                           305

Arg  Ala  Ser  Gln  Leu  Thr  Val  Ser  Ser  Leu  Gln  Cys  His  Arg  His  Lys
                        310                           315                           320

Pro  Trp  Arg  Leu  Gly  Pro  Arg  Phe  Met  Asn  Leu  Ile  Lys  Glu  Ala  Arg
                   325                      330                           335

Trp  Asp  Gly  Leu  Thr  Gly  His  Ile  Thr  Phe  Asn  Lys  Thr  Asn  Gly  Leu
              340                      345                           350

Arg  Lys  Asp  Phe  Asp  Leu  Asp  Ile  Ile  Ser  Leu  Lys  Glu  Glu  Gly  Thr
         355                           360                           365                           370

Glu  Lys  Ile  Gly  Ile  Trp  Asn  Ser  Asn  Ser  Gly  Leu  Asn  Met  Thr  Asp
                             375                           380                           385

Ser  Asn  Lys  Asp  Lys  Ser  Ser  Asn  Ile  Thr  Asp  Ser  Leu  Ala  Asn  Arg
                        390                           395                      400

Thr  Leu  Ile  Val  Thr  Thr  Ile  Leu  Glu  Glu  Pro  Tyr  Val  Met  Tyr  Arg
                        405                           410                      415

Lys  Ser  Asp  Lys  Pro  Leu  Tyr  Gly  Asn  Asp  Arg  Phe  Glu  Gly  Tyr  Cys
              420                      425                           430

Leu  Asp  Leu  Leu  Lys  Glu  Leu  Ser  Asn  Ile  Leu  Gly  Phe  Ile  Tyr  Asp
         435                           440                           445                           450

Val  Lys  Leu  Val  Pro  Asp  Gly  Lys  Tyr  Gly  Ala  Gln  Asn  Asp  Lys  Gly
                             455                           460                           465

Glu  Trp  Asn  Gly  Met  Val  Lys  Glu  Leu  Ile  Asp  His  Arg  Ala  Asp  Leu
                        470                           475                           480

Ala  Val  Ala  Pro  Leu  Thr  Ile  Thr  Tyr  Val  Arg  Glu  Lys  Val  Ile  Asp
                        485                           490                           495

Phe  Ser  Lys  Pro  Phe  Met  Thr  Leu  Gly  Ile  Ser  Ile  Leu  Tyr  Arg  Lys
              500                      505                           510

Pro  Asn  Gly  Thr  Asn  Pro  Gly  Val  Phe  Ser  Phe  Leu  Asn  Pro  Leu  Ser
         515                           520                           525                           530

Pro  Asp  Ile  Trp  Met  Tyr  Val  Leu  Leu  Ala  Cys  Leu  Gly  Val  Ser  Cys
                             535                           540                           545
```

```
Val  Leu  Phe  Val  Ile  Ala  Arg  Phe  Thr  Pro  Tyr  Glu  Trp  Tyr  Asn  Pro
               550                 555                      560

His  Pro  Cys  Asn  Pro  Asp  Ser  Asp  Val  Val  Glu  Asn  Asn  Phe  Thr  Leu
          565                      570                      575

Leu  Asn  Ser  Phe  Trp  Phe  Gly  Val  Gly  Ala  Leu  Met  Gln  Gln  Gly  Ser
     580                 585                      590

Glu  Leu  Met  Pro  Lys  Ala  Leu  Ser  Thr  Arg  Ile  Val  Gly  Gly  Ile  Trp
595                      600                 605                           610

Trp  Phe  Phe  Thr  Leu  Ile  Ile  Ile  Ser  Ser  Tyr  Thr  Ala  Asn  Leu  Ala
               615                      620                           625

Ala  Phe  Leu  Thr  Val  Glu  Arg  Met  Glu  Ser  Pro  Ile  Asp  Ser  Ala  Asp
               630                 635                      640

Asp  Leu  Ala  Lys  Gln  Thr  Lys  Ile  Glu  Tyr  Gly  Ala  Val  Arg  Asp  Gly
          645                      650                      655

Ser  Thr  Met  Thr  Phe  Phe  Lys  Ser  Lys  Ile  Ser  Thr  Tyr  Glu  Lys
     660                      665                      670

Met  Trp  Ala  Phe  Met  Ser  Ser  Arg  Gln  Gln  Thr  Ala  Leu  Val  Arg  Asn
675                      680                 685                           690

Ser  Asp  Glu  Gly  Ile  Gln  Arg  Val  Leu  Thr  Thr  Asp  Tyr  Ala  Leu  Leu
               695                      700                           705

Met  Glu  Ser  Thr  Ser  Ile  Glu  Tyr  Val  Thr  Gln  Arg  Asn  Cys  Asn  Leu
               710                 715                      720

Thr  Gln  Ile  Gly  Gly  Leu  Ile  Asp  Ser  Lys  Gly  Tyr  Gly  Val  Gly  Thr
          725                 730                      735

Pro  Ile  Gly  Ser  Pro  Tyr  Arg  Asp  Lys  Ile  Thr  Ile  Ala  Ile  Leu  Gln
     740                 745                      750

Leu  Gln  Glu  Glu  Gly  Lys  Leu  His  Met  Met  Lys  Glu  Lys  Trp  Trp  Arg
755                      760                 765                           770

Gly  Asn  Gly  Cys  Pro  Glu  Glu  Asp  Asn  Lys  Glu  Ala  Ser  Ala  Leu  Gly
               775                      780                           785

Val  Glu  Asn  Ile  Gly  Gly  Ile  Phe  Ile  Val  Leu  Ala  Ala  Ala  Gly  Leu
               790                      795                      800

Val  Leu  Ser  Val  Phe  Val  Ala  Ile  Gly  Glu  Phe  Ile  Tyr  Lys  Ser  Arg
          805                      810                      815

Lys  Asn  Asn  Asp  Ile  Glu  Gln  Val  Ser  His  Leu  Phe  Leu  Gly  Leu  Val
820                           825                 830

Ser  Leu
835
```

(2) INFORMATION FOR SEQ ID NO:18:

(i) SEQUENCE CHARACTERISTICS:
        (A) LENGTH: 849 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

```
Met  Glu  His  Gly  Thr  Leu  Leu  Ala  Gln  Pro  Gly  Leu  Trp  Thr  Arg  Asp
1              5                      10                           15

Thr  Ser  Trp  Ala  Leu  Leu  Tyr  Phe  Leu  Cys  Tyr  Ile  Leu  Pro  Gln  Thr
               20                 25                      30

Ala  Pro  Gln  Ala  Ser  Arg  Arg  Ala  Cys  Asp  Gln  Leu  Ala  Leu  Gly  Val
          35                      40                      45

Ala  Ala  Leu  Phe  Gly  Pro  Ser  His  Ser  Ser  Ser  Val  Ser  Ala  Val  Gln
```

|     |     |     |     |     | 50  |     |     |     |     | 55  |     |     |     |     | 60  |     |     |     |     |
| --- | --- | --- | --- | --- | --- | --- | --- | --- | --- | --- | --- | --- | --- | --- | --- | --- | --- | --- | --- |
| Ser | Ile | Cys | Asn | Ala | Leu | Glu | Val | Pro | His | Ile | Gln | Thr | Arg | Trp | Lys |
| 65  |     |     |     |     | 70  |     |     |     |     | 75  |     |     |     |     | 80  |
| His | Pro | Ser | Val | Asp | Asn | Lys | Asp | Leu | Phe | Tyr | Ile | Asn | Leu | Tyr | Pro |
|     |     |     |     | 85  |     |     |     |     | 90  |     |     |     |     | 95  |     |
| Asp | Tyr | Ala | Ala | Ile | Ser | Arg | Ala | Ile | Leu | Asp | Leu | Val | Leu | Tyr | Tyr |
|     |     |     | 100 |     |     |     |     | 105 |     |     |     |     | 110 |     |     |
| Asn | Trp | Lys | Thr | Val | Thr | Val | Val | Tyr | Glu | Asp | Ser | Thr | Gly | Leu | Ile |
|     |     | 115 |     |     |     |     | 120 |     |     |     |     | 125 |     |     |     |
| Arg | Leu | Gln | Glu | Leu | Ile | Lys | Ala | Pro | Ser | Arg | Tyr | Asn | Ile | Lys | Ile |
|     | 130 |     |     |     |     | 135 |     |     |     |     | 140 |     |     |     |     |
| Lys | Ile | Arg | Gln | Leu | Pro | Ser | Gly | Asn | Lys | Asp | Ala | Lys | Pro | Leu | Leu |
| 145 |     |     |     |     | 150 |     |     |     |     | 155 |     |     |     |     | 160 |
| Lys | Glu | Met | Lys | Lys | Gly | Lys | Glu | Phe | Tyr | Val | Ile | Phe | Asp | Cys | Ser |
|     |     |     |     | 165 |     |     |     |     | 170 |     |     |     |     | 175 |     |
| His | Glu | Thr | Ala | Ala | Glu | Ile | Leu | Lys | Gln | Ile | Leu | Phe | Met | Gly | Met |
|     |     |     | 180 |     |     |     |     | 185 |     |     |     |     | 190 |     |     |
| Met | Thr | Glu | Tyr | Tyr | His | Tyr | Phe | Phe | Thr | Thr | Leu | Asp | Leu | Phe | Ala |
|     |     | 195 |     |     |     |     | 200 |     |     |     |     | 205 |     |     |     |
| Leu | Asp | Leu | Glu | Leu | Tyr | Arg | Tyr | Ser | Gly | Val | Asn | Met | Thr | Gly | Phe |
|     | 210 |     |     |     |     | 215 |     |     |     |     | 220 |     |     |     |     |
| Gly | Leu | Leu | Asn | Ile | Asp | Asn | Pro | His | Val | Ser | Ile | Ile | Glu | Lys |
| 225 |     |     |     |     | 230 |     |     |     |     | 235 |     |     |     |     | 240 |
| Trp | Ser | Met | Glu | Arg | Leu | Gln | Ala | Pro | Pro | Arg | Pro | Glu | Thr | Gly | Leu |
|     |     |     |     | 245 |     |     |     |     | 250 |     |     |     |     | 255 |     |
| Leu | Asp | Gly | Met | Met | Thr | Thr | Glu | Ala | Ala | Leu | Met | Tyr | Asp | Ala | Val |
|     |     |     | 260 |     |     |     |     | 265 |     |     |     |     | 270 |     |     |
| Tyr | Met | Val | Ala | Ile | Ala | Ser | His | Arg | Ala | Ser | Gln | Leu | Thr | Val | Ser |
|     |     | 275 |     |     |     |     | 280 |     |     |     |     | 285 |     |     |     |
| Ser | Leu | Gln | Cys | His | Arg | His | Lys | Pro | Trp | Arg | Leu | Gly | Pro | Arg | Phe |
|     | 290 |     |     |     |     | 295 |     |     |     |     | 300 |     |     |     |     |
| Met | Asn | Leu | Ile | Lys | Glu | Ala | Arg | Trp | Asp | Gly | Leu | Thr | Gly | His | Ile |
| 305 |     |     |     |     | 310 |     |     |     |     | 315 |     |     |     |     | 320 |
| Thr | Phe | Asn | Lys | Thr | Asn | Gly | Leu | Arg | Lys | Asp | Phe | Asp | Leu | Asp | Ile |
|     |     |     |     | 325 |     |     |     |     | 330 |     |     |     |     | 335 |     |
| Ile | Ser | Leu | Lys | Glu | Glu | Gly | Thr | Glu | Lys | Ile | Gly | Ile | Trp | Asn | Ser |
|     |     |     | 340 |     |     |     |     | 345 |     |     |     |     | 350 |     |     |
| Asn | Ser | Gly | Leu | Asn | Met | Thr | Asp | Ser | Asn | Lys | Asp | Lys | Ser | Ser | Asn |
|     |     | 355 |     |     |     |     | 360 |     |     |     |     | 365 |     |     |     |
| Ile | Thr | Asp | Ser | Leu | Ala | Asn | Arg | Thr | Leu | Ile | Val | Thr | Thr | Ile | Leu |
|     | 370 |     |     |     |     | 375 |     |     |     |     | 380 |     |     |     |     |
| Glu | Glu | Pro | Tyr | Val | Met | Tyr | Arg | Lys | Ser | Asp | Lys | Pro | Leu | Tyr | Gly |
| 385 |     |     |     |     | 390 |     |     |     |     | 395 |     |     |     |     | 400 |
| Asn | Asp | Arg | Phe | Glu | Gly | Tyr | Cys | Leu | Asp | Leu | Leu | Lys | Glu | Leu | Ser |
|     |     |     |     | 405 |     |     |     |     | 410 |     |     |     |     | 415 |     |
| Asn | Ile | Leu | Gly | Phe | Ile | Tyr | Asp | Val | Lys | Leu | Val | Pro | Asp | Gly | Lys |
|     |     |     | 420 |     |     |     |     | 425 |     |     |     |     | 430 |     |     |
| Tyr | Gly | Ala | Gln | Asn | Asp | Lys | Gly | Glu | Trp | Asn | Gly | Met | Val | Lys | Glu |
|     |     | 435 |     |     |     |     | 440 |     |     |     |     | 445 |     |     |     |
| Leu | Ile | Asp | His | Arg | Ala | Asp | Leu | Ala | Val | Ala | Pro | Leu | Thr | Ile | Thr |
|     | 450 |     |     |     |     | 455 |     |     |     |     | 460 |     |     |     |     |
| Tyr | Val | Arg | Glu | Lys | Val | Ile | Asp | Phe | Ser | Lys | Pro | Phe | Met | Thr | Leu, |
| 465 |     |     |     |     | 470 |     |     |     |     | 475 |     |     |     |     | 480 |

-continued

| | | | | | | | | | | | | | |
|---|---|---|---|---|---|---|---|---|---|---|---|---|---|
| Gly | Ile | Ser | Ile | Leu 485 | Tyr | Arg | Lys | Pro | Asn 490 | Gly | Thr | Asn | Pro | Gly 495 | Val |
| Phe | Ser | Phe | Leu 500 | Asn | Pro | Leu | Ser | Pro 505 | Asp | Ile | Trp | Met | Tyr 510 | Val | Leu |
| Leu | Ala | Cys 515 | Leu | Gly | Val | Ser | Cys 520 | Val | Leu | Phe | Val | Ile 525 | Ala | Arg | Phe |
| Thr | Pro 530 | Tyr | Glu | Trp | Tyr | Asn 535 | Pro | His | Pro | Cys | Asn 540 | Pro | Asp | Ser | Asp |
| Val 545 | Val | Glu | Asn | Asn | Phe 550 | Thr | Leu | Leu | Asn | Ser 555 | Phe | Trp | Phe | Gly | Val 560 |
| Gly | Ala | Leu | Met | Gln 565 | Gln | Gly | Ser | Glu | Leu 570 | Met | Pro | Lys | Ala | Leu 575 | Ser |
| Thr | Arg | Ile | Val 580 | Gly | Gly | Ile | Trp | Trp 585 | Phe | Phe | Thr | Leu | Ile 590 | Ile | Ile |
| Ser | Ser | Tyr 595 | Thr | Ala | Asn | Leu | Ala 600 | Ala | Phe | Leu | Thr | Val 605 | Glu | Arg | Met |
| Glu | Ser 610 | Pro | Ile | Asp | Ser | Ala 615 | Asp | Asp | Leu | Ala | Lys 620 | Gln | Thr | Lys | Ile |
| Glu 625 | Tyr | Gly | Ala | Val | Arg 630 | Asp | Gly | Ser | Thr | Met 635 | Thr | Phe | Phe | Lys | Lys 640 |
| Ser | Lys | Ile | Ser | Thr 645 | Tyr | Glu | Lys | Met | Trp 650 | Ala | Phe | Met | Ser | Ser 655 | Arg |
| Gln | Gln | Thr | Ala 660 | Leu | Val | Arg | Asn | Ser 665 | Asp | Glu | Gly | Ile | Gln 670 | Arg | Val |
| Leu | Thr | Thr 675 | Asp | Tyr | Ala | Leu | Leu 680 | Met | Glu | Ser | Thr | Ser 685 | Ile | Glu | Tyr |
| Val | Thr 690 | Gln | Arg | Asn | Cys | Asn 695 | Leu | Thr | Gln | Ile | Gly 700 | Gly | Leu | Ile | Asp |
| Ser 705 | Lys | Gly | Tyr | Gly | Val 710 | Gly | Thr | Pro | Ile | Gly 715 | Ser | Pro | Tyr | Arg | Asp 720 |
| Lys | Ile | Thr | Ile | Ala 725 | Ile | Leu | Gln | Leu | Gln 730 | Glu | Glu | Gly | Lys | Leu 735 | His |
| Met | Met | Lys | Glu 740 | Lys | Trp | Trp | Arg | Gly 745 | Asn | Gly | Cys | Pro | Glu 750 | Glu | Asp |
| Asn | Lys | Glu 755 | Ala | Ser | Ala | Leu | Gly 760 | Val | Glu | Asn | Ile | Gly 765 | Gly | Ile | Phe |
| Ile | Val 770 | Leu | Ala | Ala | Gly | Leu 775 | Val | Leu | Ser | Val | Phe 780 | Val | Ala | Ile | Gly |
| Glu 785 | Phe | Ile | Tyr | Lys | Ser 790 | Arg | Lys | Asn | Asn | Asp 795 | Ile | Glu | Gln | Cys | Leu 800 |
| Ser | Phe | Asn | Ala | Ile 805 | Met | Glu | Glu | Leu | Gly 810 | Ile | Ser | Leu | Lys | Asn 815 | Gln |
| Lys | Lys | Ile | Lys 820 | Lys | Lys | Ser | Arg | Thr 825 | Lys | Gly | Lys | Ser | Ser 830 | Phe | Thr |
| Ser | Ile | Leu 835 | Thr | Cys | His | Gln | Arg 840 | Arg | Thr | Gln | Arg | Lys 845 | Glu | Thr | Val |
| Ala | | | | | | | | | | | | | | | |